United States Patent
Kondo et al.

(10) Patent No.: US 10,106,757 B2
(45) Date of Patent: Oct. 23, 2018

(54) IONIC LIQUID, LUBRICANT, AND MAGNETIC RECORDING MEDIUM

(71) Applicant: DEXERIALS CORPORATION, Shinagawa-ku, Tokyo (JP)

(72) Inventors: Hirofumi Kondo, Tokyo (JP); Kouki Hatsuda, Tokyo (JP); Nobuo Tano, Tokyo (JP); Pankaj Baghel, Tokyo (JP)

(73) Assignee: DEXERIALS CORPORATION, Shinagawa-Ku, Tokyo (JP)

( * ) Notice: Subject to any disclaimer, the term of this patent is extended or adjusted under 35 U.S.C. 154(b) by 0 days.

(21) Appl. No.: 15/485,559

(22) Filed: Apr. 12, 2017

(65) Prior Publication Data
US 2017/0298285 A1 Oct. 19, 2017

(30) Foreign Application Priority Data
Apr. 13, 2016 (JP) ................. 2016-080576

(51) Int. Cl.
*C10M 105/72* (2006.01)
*C10M 105/70* (2006.01)
(Continued)

(52) U.S. Cl.
CPC ......... *C10M 105/72* (2013.01); *C07C 309/06* (2013.01); *C07D 233/58* (2013.01);
(Continued)

(58) Field of Classification Search
CPC .......... C10M 105/70; C10M 2240/204; C10M 105/72; C10M 2215/224; C10M 2219/044;
(Continued)

(56) References Cited

U.S. PATENT DOCUMENTS

2008/0144219 A1* 6/2008 Burns ................. C10M 169/04
360/135
2010/0084597 A1* 4/2010 Schwab ............. B01D 19/0404
252/8.86
(Continued)

FOREIGN PATENT DOCUMENTS

JP 2581090 B2 2/1997
JP 2629725 B2 7/1997
(Continued)

OTHER PUBLICATIONS

Anderson, Jared L. et al., "Structure and Properties of High Stability Geminal Dicationic Ionic Liquids", J. Am. Chem. Soc., 2005 (month unknown), vol. 127, No. 2, pp. 593-604.
(Continued)

*Primary Examiner* — James C Goloboy
(74) *Attorney, Agent, or Firm* — Buchanan, Ingersoll & Rooney PC

(57) ABSTRACT

A lubricant, which includes an ionic liquid including a conjugate base and a conjugate acid, wherein the conjugate acid is represented by General Formula (A) below, and wherein a pKa of an acid that is a source of the conjugate base in acetonitrile is 10 or less,

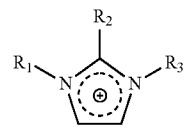

General Formula (A)

where, in General Formula (A), $R_1$, $R_2$, and $R_3$ are each independently a group including a hydrocarbon group, with
(Continued)

the proviso that at least one of the hydrocarbon groups in $R_1$, $R_2$, and $R_3$ is a straight-chain hydrocarbon group having 6 or greater carbon atoms.

9 Claims, 3 Drawing Sheets

(51) Int. Cl.
    *C07C 309/06* (2006.01)
    *C07D 233/58* (2006.01)
    *G11B 5/725* (2006.01)

(52) U.S. Cl.
    CPC ........... *C10M 105/70* (2013.01); *G11B 5/725* (2013.01); *C10M 2215/224* (2013.01); *C10M 2219/044* (2013.01); *C10N 2220/04* (2013.01); *C10N 2240/204* (2013.01)

(58) Field of Classification Search
    CPC .......... C10N 2220/04; C10N 2240/204; C07C 233/58; C07C 309/06; G11B 5/725
    See application file for complete search history.

(56) References Cited

U.S. PATENT DOCUMENTS

2015/0291515 A1* 10/2015 Uerdingen ............ C07C 309/10
    508/403
2015/0353558 A1    12/2015 Kondo et al.

FOREIGN PATENT DOCUMENTS

WO    WO 2005/068589 A1    7/2005
WO    WO 2014/104342 A1    7/2014

OTHER PUBLICATIONS

Dzyuba, Sergie V. et al., "Influence of Structural Variations in 1-Alkyl(aralkyl)-3-Methylimidazolium Hexafluorophosphates and Bis(trifluoromethylsulfonyl)imides on Physical Properties of the Ionic Liquids", European Journal of Chemical Physics and Physical Chemistry, Chemistry Physics, Feb. 15, 2002, vol. 3, No. 2, pp. 161-166.
Gui, Jing, "Tribology challenges for head-disk interface toward 1Tb/in$^2$," IEEE Transactions on Magnetics, Mar. 2003, vol. 39, No. 2, pp. 716-721.
Kondo, Hirofumi et al., "Comparison of an Amide and Amine Salt as Friction Modifiers for a Magnetic Thin Film Medium", Tribology Transactions, Jan. 1994, vol. 37, No. 1, pp. 99-104, ISSN: 0569-8197.
Kondo, Hirofumi et al., "Novel Lubricants for Magnetic Thin Film Media", Journal of the Magnetic Society of Japan, 1989 (month unknown), vol. 13, Suppl. No. SI, pp. 213-218.
Kondo, Hirofumi et al., "Frictional Properties of Novel Lubricants for Magnetic Thin Film Media", IEEE Transactions on Magnetics, Sep. 1990, vol. 26, No. 5, pp. 2691-2693, ISSN: 0018-9464.
Kondo, Hirofumi et al., "Novel Ionic Lubricants for Magnetic Thin Film" Media, IEEE Transactions on Magnetics, Jul. 2013, vol. 49, No. 7, pp. 3756-3759.
Kondo, Hirofumi et al., "New Ionic Lubricants for Magnetic Thin-Film Media", IEEE Transactions on Magnetics, Nov. 2014, vol. 50, No. 11, Article#: 3302504, 4 pages.
Marchon, Bruno et al., "The head-disk interface roadmap to an areal density of 4 Tbit/in$^2$", Advances in Tribology, vol. 2013, Article ID 521086, pp. 1-9.
Marchon, Bruno et al., "Magnetic spacing trends: From LMR to PMR and beyond," IEEE Transactions on Magnetics, Oct. 2009, vol. 45, No. 10, pp. 3608-3611.
Mate, C. Matthe et al., "Will the numbers add up for sub-7-nm magnetic spacings? Future metrology issues for disk drive lubricants, overcoats, and topographies," IEEE Transactions on Magnetics, Feb. 2005, vol. 41, No. 2, pp. 626-631.
Miran, Muhammed Shah et al., "Physicochemical Properties Determined by ApKa for Protic Ionic Liquids Based on an Organic Super-strong Base with Various Bronsted Acids", Phys. Chem. Chem. Phys., 2012 (month unknown), vol. 14, pp. 5178-5186.
Waltman, R. J. et al., "Studies on the interactions between ZDOL perfluoropolyether lubricant and the carbon overcoat of rigid magnetic media", Tribology Letters, 1998 (month unknown), vol. 4, Issue 3, pp. 267-275.
Yoshizawa, Masahiro et al., "Ionic Liquids by Proton Transfer: Vapor pressure, Conductivity, and the Relevance of ApKa from Aqueous Solutions", J. Am. Chem. Soc., 2003 (month unknown), vol. 125, No. 50, pp. 15411-15419.

* cited by examiner

IONIC LIQUID, LUBRICANT, AND MAGNETIC RECORDING MEDIUM

BACKGROUND OF THE INVENTION

Field of the Invention

The present invention relates to an ionic liquid, a lubricant containing the ionic liquid, and a magnetic recording medium using the lubricant.

Description of the Related Art

Conventionally, in a thin film magnetic recording medium, a lubricant is applied onto a surface of a magnetic layer for the purpose of reducing frictions between a magnetic head and the surface of the magnetic recording medium, or reducing abrasion. In order to avoid adhesion, such as sticktion, an actual film thickness of the lubricant is of a molecular order. Accordingly, it is not exaggeration to say that the most important thing for a thin film magnetic recording medium is to select a lubricant having excellent abrasion resistance in any environment.

During a life of a magnetic recording medium, it is important that a lubricant is present on a surface of the medium without causing desorption, spin-off, and chemical deteriorations. Making the lubricant present on a surface of a medium is more difficult, as the surface of the thin film magnetic recording medium is smoother. This is because the thin film magnetic recording medium does not have an ability of replenishing a lubricant as with a coating-type magnetic recording medium.

In the case where an adhesion force between a lubricant and a protective film disposed at a surface of a magnetic layer is weak, moreover, a film thickness of the lubricant is reduced during heating or sliding hence accelerating abrasion. Therefore, a large amount of the lubricant is required. The large amount of the lubricant is the mobile lubricant, and therefore a function of replenishing the lost lubricant can be provided. However, an excessive amount of the lubricant makes the film thickness of the lubricant larger than the surface roughness. Therefore, a problem associated with adhesion arises, and in a crucial case, sticktion arises to cause driving failures.

As illustrated in FIG. 1, although an increase rate of an areal density of a hard disk drive of a product have been reduced in the last few years, the increase rate has reached an annual rate of 25%, and has nearly reaches 4 $Tb/in^2$, which is one of targets, in Advances in Tribology Volume 2013, Article ID 521086. As illustrated in FIG. 2, it has been understood that a distance between head disk interfaces relative to an increase in the recording density reduces, but there is a need to always improve reliability corresponding to the reduction in the distance, which can be described, for example, in non-patent literatures below. (C. M. Mate, Q. Dai, R. N. Payne, B. E. Knigge, and P. Baumgart, "Will the numbers add up for sub-7-nm magnetic spacings? Future metrology issues for disk drive lubricants, overcoats, and topographies," IEEE Transactions on Magnetics, vol. 41, no. 2, pp. 626-631, 2005., B. Marchon and T. Olson, "Magnetic spacing trends: from LMR to PMR and beyond," IEEE Transactions on Magnetics, vol. 45, no. 10, pp. 3608-3611, 2009., J. Gui, "Tribology challenges for head-disk interface toward 1 $Tb/in^2$," IEEE Transactions on Magnetics, vol. 39, no. 2, pp. 716-721, 2003.).

A current recording density is about 1 $Tb/in^2$, spacing is about 6 nm, and a thickness of a lubricant is 0.8 nm. The thickness of the lubricant needs to be reduced at the prospective recording density of 4 $Tb/in^2$. In order to reduce a thickness of a film of a PFPE lubricant commonly used in the art, however, a molecular weight of the PFPE lubricant needs to be decreased. The smaller molecular weight of the PFPE lubricant has a problem that thermal stability is deteriorated. It has been understood that the above-described problems associated with reliability have not be sufficiently solved with common perfluoropolyether (PFPE)-based lubricants.

Particularly for a thin film magnetic recording medium having high surface smoothness, a novel lubricant is designed at a molecular level, and synthesized to solve the above-described trade-off. Moreover, there are a number of reports regarding lubricity of PFPE. As described, lubricants are very important in magnetic recording media.

Chemical structures of typical PFPE-based lubricants are depicted in Table 1.

TABLE 1

Fomblin-based lubricants

| | $X-CF_2(OCF_2CF_2)_n(OCF_2)_mOCF_2-X (0.5 < n/m < 1)$ |
|---|---|
| Z | $X = -OCF_3$ |
| Z-DOL | $X = -CH_2OH$ |
| Z-DIAC | $X = -COOH$ |
| Z-Tetraol | $X = -CH_2OCH_2CHCH_2OHOH$ |
| AM2001 | $X = -CH_2OCH_2-\text{(benzodioxole group)}$ |

Other lubricants

A2OH    $HOCH_2CF_2(OCF_2CF_2)_n(OCF_2)_mOCF_2CH_2O-[\text{triazine}-O-\text{(CF}_3\text{-phenyl)}]_5$ Mono    $F-(CF_2CF_2CF_2O)_1-CF_2CF_2CH_2-N(C_3H_7)_2$ Z-DOL in Table 1 is one of lubricants typically used for thin-film magnetic recording media. Moreover, Z-tetraol (ZTMD) is a lubricant, in which a functional hydroxyl group is further introduced into a main chain of PFPE, and it has been reported that use of Z-tetraol enhances reliability of a drive while reducing a space at an interface between a head and a medium. It has been reported that A20H suppresses decomposition of the PFPE main chain with Lewis acid or Lewis base, and improves tribological properties. On the other hand, it has been reported that Mono has a different polymer main chain and different polar groups to those of the PFPE, and the polymer main chain and polar groups of Mono are respectively poly-n-propyloxy, and amine, and Mono reduces adhesion interactions at near contact.

However, a typical solid lubricant, which has a high melting point and is considered thermally stable, disturbs an electromagnetic conversion process that is extremely highly sensitive, and moreover, an abrasion powder scraped by a head is generated on a running track. Therefore, abrasion properties are deteriorated. As described above, the liquid lubricant has mobility that enables to move the adjacent lubricant layer to replenish the lubricant removed due to abrasion by the head. However, the lubricant is span-off from a surface of the disk especially at a high temperature during driving of the disk, because of the mobility of the lubricant, and thus the lubricant is reduced. As a result, a protection function is lost. Accordingly, a lubricant having a high viscosity and low volatility is suitably used, and use of such a lubricant enables to prolong a service life of a disk drive with suppressing an evaporation rate.

Considering the above-described lubricating systems, requirements for a low-friction and low-abrasion lubricant used for thin film magnetic recording media are as follows.
(1) Low volatility.
(2) Low surface tension for a surface filling function.
(3) Interaction between terminal polar groups and a surface of a disk.
(4) High thermal and oxidization stability in order to avoid decomposition or reduction over a service period.
(5) Chemically inactive with metals, glass, and polymers, and no abrasion powder generated from a head or a guide.
(6) No toxicity and no flammability.
(7) Excellent boundary lubricating properties.
(8) Soluble with organic solvents.

Recently, an ionic liquid has been attracted attentions as one of solvents for synthesis of organic or inorganic materials and being friendly to the environments in the fields of electricity storage materials, a separation technology, and a catalyst technology. The ionic liquid is roughly classified as a molten salt having a low melting point. The ionic liquid is typically a molten salt having a melting point of 100° C. or lower, among the above-mentioned molten salts. The important properties of the ionic liquid used as a lubricant are low volatility, inflammability, thermal stability, and an excellent dissolving performance.

For example, abrasion and wear of a surface of a metal or ceramic may be reduced by using a certain ionic liquid compared to a conventional hydrocarbon-based lubricant. For example, there is a report that, in the case where an imidazole cation-based ionic liquid is synthesized by substituting with a fluoroalkyl group, and tetrafluoroboric acid salt or hexafluorophosphoric acid salt of alkyl imidazolium is used for steel, aluminium, copper, single crystal $SiO_2$, silicon, or sialon ceramics (Si—Al—O—N), tribological properties more excellent than those of cyclic phosphazene (X-1P) or PFPE are exhibited. Moreover, there is a report that an ammonium-based ionic liquid reduces frictions more than a base oil in the region of elastohydrodynamic to boundary lubrication. Moreover, effects of the ionic liquid as an additive for a base oil have been studied, and a chemical or tribochemical reaction of the ionic liquid has been researched to understand lubricating systems. However, there are almost no application examples of the ionic liquid to magnetic recording media.

Among the ionic liquids, a perfluorooctanoic acid alkyl ammonium salt is a protic ionic liquid (PIL), and has been reported as having a significant effect of reducing frictions of magnetic recording media compared to Z-DOL mentioned above (see, for example, Japanese Patent Nos. 2581090 and 2629725, Kondo, H., Seto, J., Haga. S., Ozawa, K. (1989) Novel Lubricants for Magnetic Thin Film Media, Magnetic Soc. Japan, Vol. 13, Suppl. No. 51, pp. 213-218, Kondo, H., Seki, A., Watanabe, H., & Seto, J., (1990). Frictional Properties of Novel Lubricants for Magnetic Thin Film Media, IEEE Trans. Magn. Vol. 26, No. 5, (September 1990), pp. 2691-2693, ISSN: 0018-9464, Kondo, H., Seki, A., & Kita, A., (1994a). Comparison of an Amide and Amine Salt as Friction Modifiers for a Magnetic Thin Film Medium. Tribology Trans. Vol. 37, No. 1, (January 1994), pp. 99-104, ISSN: 0569-8197).

However, the above-mentioned perfluorocarboxylic acid ammonium salts have weak interaction between a cation and an anion in the reaction represented by the following reaction formula (A). According to Le Chatelier's principle, the equilibrium of the reaction is sifted to the left side at a high temperature, and the perfluorocarboxylic acid ammonium salt becomes a dissociated neutral compound and hence thermal stability is deteriorated. Specifically, protons are transferred at a high temperature, the equilibrium is sifted to neutral substance and dissociation occurs (see, for example, Yoshizawa, M., Xu, W., Angell, C. A., Ionic Liquids by Proton Transfer: Vapor pressure, Conductivity, and the Relevance of ΔpKa from Aqueous Solutions, J. Am. Chem. Soc., Vol. 125, pp. 15411-15419 (2003)).

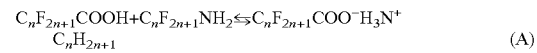

$$C_nF_{2n+1}COOH + C_nF_{2n+1}NH_2 \leftrightarrows C_nF_{2n+1}COO^-H_3N^+C_nH_{2n+1} \quad (A)$$

Meanwhile, the limit of a surface recording density of a hard disk is said to be from 1 Tb/in$^2$ to 2.5 Tb/in$^2$. Currently, the surface recording density is getting close to the limit, but developments of technology for increasing capacities have been actively conducted with a reduction in particle size of magnetic particles as a premise. As the technology for increasing capacities, there are a reduction in an effective flying height and introduction of Shingle Write (BMP).

Moreover, there is "thermally-assisted magnetic recording (heat assisted magnetic recording)" as the next-generation recording technology. The outline of the thermally-assisted magnetic recording is illustrated in FIG. 3. In FIG. 3, the referential numeral 1 is laser light, the referential numeral 2 is near field light, the referential numeral 3 is a recording head (PMR element), and the referential numeral 4 is a reproducing head (TMR element). The problems of the thermally-assisted magnetic recording include a deterioration of durability due to evaporation or deterioration of a lubricant on a surface of a magnetic layer because a recording area is heated by laser during recording and reproducing. Even though it is a short period, there is a possibility that a thin film magnetic recording medium is exposed to a high temperature, which is 400° C. or higher, in thermally-assisted magnetic recording. Therefore, thermal stability of a lubricant generally used for thin film magnetic recording media, such as Z-DOL and Z-TETRAOL, is considered.

A protic ionic liquid forms ions as described above, and is typically a material having high thermal stability. The equilibrium of the protic ionic liquid is represented by Scheme 1 below.

Scheme 1 Scheme of acid-base reaction $$HA + H_2O \rightleftharpoons H_3O^+ + A^-$$

$$B + H_2O \rightleftharpoons HB^+ + OH^-$$

$$A^- + HB^+ \rightarrow A^-HB^+$$

$$\overline{HA + B + 2H_2O \rightleftharpoons A^-HB^+ + H_3O^+ + OH^-}$$

In Scheme 1, HA is Bronsted acid and B is Bronsted base. The acid (HA) and the base (B) are reacted as in Scheme 1 to generate a salt ($A^-HB^+$).

In Scheme 1, a dissociation constant $K_{a1}$ of the acid and a dissociation constant $K_{b2}$ of the base can be represented by Scheme 2 below in the form including the density.

Scheme 2 Relationship of acid and base dissociation constants

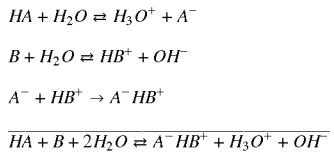

$$K_{a1} = \frac{[A^-][H_3O^+]}{[HA]}$$

$$K_{b2} = \frac{[HB^+][OH^-]}{[B]}$$

The $K_{a1}$ and $K_{b2}$ largely differ depending on a substance. In some cases, the $K_{a1}$ and $K_{b2}$ may be large digits, which is inconvenient for handling. Therefore, it is often represented with a negative logarithm. Specifically, the acid dissociation constant is determined as $-\log_{10} K_{a1} = pK_{a1}$ as represented by Scheme 3 below. Clearly, acidity is stronger, as the $pK_{a1}$ is smaller.

A difference $\Delta pKa$ of the acid dissociation constants of the acid and the base is discussed. The acid-base reaction is influenced by both acidity of the acid and basicity of the base (or acidity of conjugate acid of the base), and the difference $\Delta pKa$ in the acidity of the acid and base is represented by Scheme 3 below.

Scheme 3 Relationship of pKa of acid and base $$pK_{a1} = -\log\frac{[A^-][H_3O^+]}{[HA]}$$

$$pK_{b2} = -\log\frac{[HB^+][OH^-]}{[B]}$$

$$pK_{a2} = 14 - pK_{b2} = 14 + \log\frac{[BH^+][OH^-]}{[B]}$$

$$\Delta pK_a = pK_{a2} - pK_{a1} = -pK_{a1} - pK_{b2} + 14$$

$$= \log\frac{[A^-][BH^+][H_3O^+][OH^-]}{[HA][B]}$$

$$= \log\frac{[A^-][HB^+]}{[HA].[B]} = \log\frac{[A^-HB^+]}{[HA][B]}$$

It is indicated that the $\Delta pKa$ increases, as the base concentration [$A^-HB^+$] increases relative to the acid concentration and the base concentration.

Meanwhile, Yoshizawa et al. have reported that proton transfer tends to occur when a difference ($\Delta pKa$) of pKa of acid and base is 10 or greater, $$[AH]+[B] \leftrightarrow [A^-HB^+]$$

the equilibrium of the formula above is sifted to the ion side (right side), and stability is enhanced further (see, for example, Yoshizawa, M., Xu, W., Angell, C. A., Ionic Liquids by Proton Transfer: Vapor pressure, Conductivity, and the Relevance of $\Delta pKa$ from Aqueous Solutions, J. Am. Chem. Soc., Vol. 125, pp. 15411-15419 (2003)). Moreover, Watanabe et al. has reported that proton transfer and thermal stability of a protic ionic liquid largely depend on $\Delta pKa$, and thermal stability of the ionic liquid is significantly improved by using the acid with which $\Delta pKa$ is 15 or greater when DBU (1,8-diazabicyclo[5,4,0]undec-7-ene) is used as a base (see, for example, Miran, M. S., Kinoshita, H., Yasuda, T., Susan, M. A. B. H., Watanabe, M., Physicochemical Properties Determined by $\Delta pKa$ for Protic Ionic Liquids Based on an Organic Super-strong Base with Various Bronsted Acids, Phys. Chem. Chem. Phys., Vol. 14, pp. 5178-5186 (2012)). Moreover, Kondo et al. have reported that a perfluorooctanesulfonic acid octadecyl ammonium salt-based protic ionic liquid having large $\Delta pKa$ improves durability of a magnetic recording medium (see, for example, Hirofumi Kondo, Makiya Ito, Koki Hatsuda, Kyung Sung Yun and Masayoshi Watanabe, "Novel Ionic Lubricants for Magnetic Thin Film" Media, IEEE TRANSACTIONS ON MAGNETICS, VOL. 49, NO. 7, pp. 3756-3759, July (2013), WO 2014/104342). In the recent report of Kondo et al. related to thermal resistance of an ionic liquid, it has been reported that a decomposition temperature increases with up to certain degree of $\Delta pKa$, and the decomposition temperature is not increased any further even when $\Delta pKa$ is increased from the above-described point (see, for example, Hirofumi Kondo, Makiya Ito, Koki Hatsuda, Nobuo Tano, KyungSung Yun and Masayoshi Watanabe, IEEE International magnetic conference Dresden, Germany, May 4-8, 2014, and Hirofumi Kondo, Makiya Ito, Koki Hatsuda, Nobuo Tano, Kyung Sung Yun and Masayoshi Watanabe, IEEE Trans. Magn., 2014, Vol. 50, Issue 11, Article#: 3302504). Moreover, it is reported that a pyrrolidinium-based ionic liquid including germinal dication may improve thermal resistance more than a typical ionic liquid of monocation (see Anderson, J. L., Ding R., Ellern A., Armstrong D. W., "Structure and Properties of High Stability Geminal Dicationic Ionic Liquids", J. Am. Chem. Soc., 2005, 127, 593-604). As disclosed in Anderson, J. L., Ding R., Ellern A., Armstrong D. W., "Structure and Properties of High Stability Geminal Dicationic Ionic Liquids", J. Am. Chem. Soc., 2005, 127, 593-604., however, a relationship between a molecular structure constituting the pyrrolidinium-based ionic liquid and physical or chemical characteristics has not been fully understood yet. A combination of a cation and an anion largely influences on physical or chemical characteristics of an ionic liquid. A variety of the anion site is many, but the relationship is not clear unless the cation is a cation structurally similar to the anion (see, for example, Dzyuba, S. V.; Bartsch, R. A., "Influence of Structural Variations in 1-Alkyl (aralkyl)-3-Methylimidazolium Hexafluorophosphates and Bis(trifluoromethylsulfonyl)imides on Physical Properties of the Ionic Liquids, Chem. Phys. Phys. Chem. 2002, 3, 161-166). For example, viscosity of the liquid increases, as hydrogen bonding strength of halogen is stronger (Cl>Br>I). However, the method for increasing the viscosity is not limited to the increase in the hydrogen bonding strength. For example, the viscosity can be increased by varying an alkyl chain of imidazole. Similarly, the combination of the anion and cation influences melting point, surface tension, and thermal stability, but a wide range of researches has not been conducted on an effect of the anion. Accordingly, it is possible to change physical or chemical characteristics of an ionic liquid by with a combination of cations or anions, but it is difficult to predict.

In the case where the lubricants for hard disks presented in Table 1 are considered, a polar group, such as a hydroxyl group, is introduced at a terminal in order to enhance interaction with a surface of a medium. Such a hydroxyl group reacts with the surface of the medium to be fixed on the surface as a result of a heat treatment. As a result, thermal stability is improved. Moreover, there is also an effect of reducing polar site components of surface energy because the hydroxyl group is bonded (see R. J. Waltman, D. J. Pocker, G. W. Tyndall, Studies on the interactions between ZDOL perfluoropolyether lubricant and the carbon overcoat of rigid magnetic media, Tribology Letters 1998, Volume 4, Issue 3, pp. 267-275).

Meanwhile, long-chain fatty acids or esters of long-chain fatty acids have been used as lubricants known in the art. In the case where a lubricant is used in combination with an ionic liquid, the ionic liquid needs to have excellent solubility to a hydrocarbon-based solvent used for the lubricant.

SUMMARY OF THE INVENTION

The present invention is proposed based on the above-described situations in the art, and provides an ionic liquid having excellent solubility of hydrocarbon-based solvents, and has lubricity at a high temperature, a lubricant having excellent solubility to hydrocarbon-based solvent and excellent lubricity at a high temperature, and a recording medium having excellent practical properties.

Means for solving the above-described problems are as follows.

<1> A lubricant including:
an ionic liquid including a conjugate base and a conjugate acid, wherein the conjugate acid is represented by General Formula (A) below, and wherein a pKa of an acid that is a source of the conjugate base in acetonitrile is 10 or less,

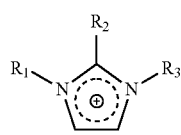

General Formula (A)

where, in General Formula (A), $R_1$, $R_2$, and $R_3$ are each independently a group including a hydrocarbon group, with the proviso that at least one of the hydrocarbon groups in $R_1$, $R_2$, and $R_3$ is a straight-chain hydrocarbon group having 6 or greater carbon atoms.

<2> The lubricant according to <1>,
wherein the conjugate base is represented by General Formula (X) or General Formula (Y) below,

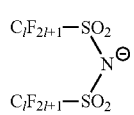

General Formula (X)

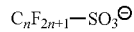

General Formula (Y)

where, in General Formula (X), l is an integer of 1 or greater but 12 or less, and
where, in General Formula (Y), n is an integer of 1 or greater but 12 or less.

<3> A magnetic recording medium including:
a non-magnetic support;
a magnetic layer disposed on the non-magnetic support; and
the lubricant according to <1> or <2>, disposed on the magnetic layer.

<4> An ionic liquid including:
a conjugate base; and
a conjugate acid,
wherein the conjugate acid is represented by General Formula (A) below, and
wherein a pKa of an acid that is a source of the conjugate base in acetonitrile is 10 or less,

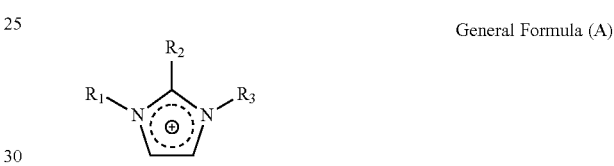

General Formula (A)

where, in General Formula (A), $R_1$, $R_2$, and $R_3$ are each independently a group including a hydrocarbon group, with the proviso that at least one of the hydrocarbon groups in $R_1$, $R_2$, and $R_3$ is a straight-chain hydrocarbon group having 6 or greater carbon atoms.

<5> The ionic liquid according to <4>,
wherein the conjugate base is represented by General Formula (X) or General Formula (Y) below,

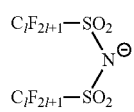

General Formula (X)

General Formula (Y)

where, in General Formula (X), l is an integer of 1 or greater but 12 or less, and
where, in General Formula (Y), n is an integer of 1 or greater but 12 or less.

According to the present invention, thermal stability of a lubricant is improved with preventing evaporation or thermal decomposition of the lubricant, excellent solubility to hydrocarbon-based solvents is obtained, and excellent lubricity can be maintained over a long period of time. When the lubricant is used for a magnetic recording medium, moreover, excellent lubricity can be obtained, and practical properties, such as running performances, abrasion resistance, and durability, can be improved.

DETAILED DESCRIPTION OF THE INVENTION

Figure 1:
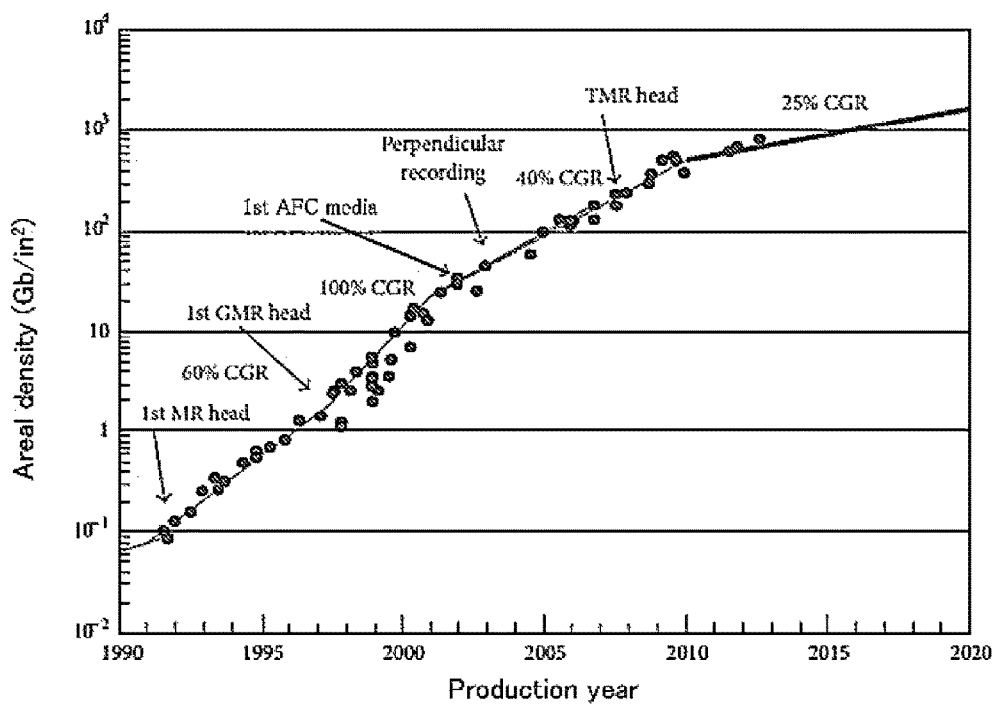
FIG. 1 is a graph presenting a transition and prediction of an in-plane recording density of a hard disk drive.
Figure 2:
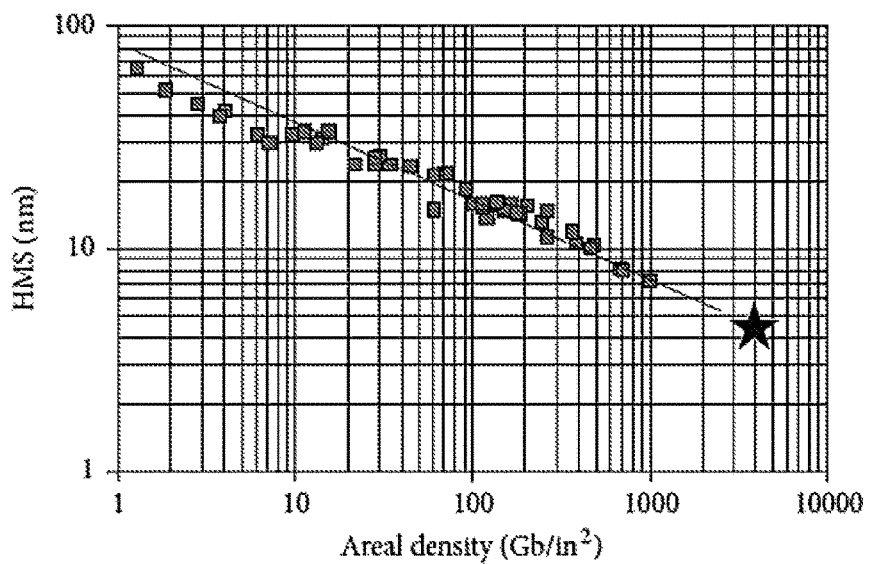
FIG. 2 is a road map of a head media spacing (HMS) relative to an in-plane recording density of a hard disk.
Figure 3:
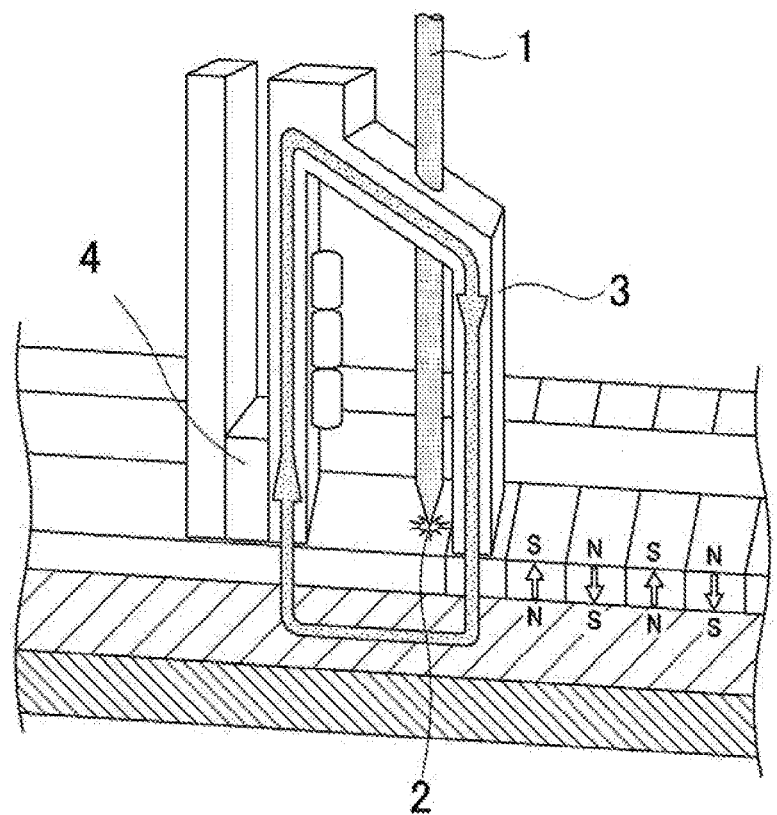
FIG. 3 is a schematic view illustrating thermally-assisted magnetic recording.

Embodiments of the present invention are specifically described with reference to drawing hereinafter in the following order.
1. Lubricant and ionic liquid
2. Magnetic recording medium
3. Examples <1. Lubricant and Ionic Liquid>

A lubricant described as one embodiment of the present invention includes an ionic liquid including a conjugate acid and a conjugate base.

An ionic liquid described as one embodiment of the present invention includes a conjugate acid and a conjugate base.

In the ionic liquid, the conjugate acid is represented by General Formula (A) below.

A pKa of an acid that is a source of the conjugate base in acetonitrile is 10 or less.

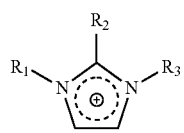

General Formula (A)

In General Formula (A), $R_1$, $R_2$, and $R_3$ are each independently a group including a hydrocarbon group, with the proviso that at least one of the hydrocarbon groups in $R_1$, $R_2$, and $R_3$ is a straight-chain hydrocarbon group having 6 or greater carbon atoms.

The ionic liquid according to the present embodiment includes a conjugate acid and a conjugate base, and a pKa of an acid that is a source of the conjugate base in acetonitrile is 10 or less. Therefore, the ionic liquid has strong bonds between ions, and can exhibit excellent thermal stability. Since the conjugate acid has a structure represented by General Formula (A), moreover, the ionic liquid has excellent solubility to hydrocarbon-based solvents. The solubility to hydrocarbon-based solvents means that the ionic liquid can exhibit an effect as an additive because compatibility is improved considering that a material widely used as a lubricant is long-chain fatty acid or ester of long-chain fatty acid.

When the ionic liquid has excellent solubility to fluorine-based solvents, moreover, there is an advantage that a production line of magnetic recording media does not need to be explosion proof.

The pKa is 10 or less, which is a strong acid, and is preferably 6.0 or less.

The lower limit of the pKa is not particularly limited and may be appropriately selected depending on the intended purpose, but the pKa is preferably −5.0 or greater.

In the present specification, "pKa" is an acid dissociation constant, and is an acid dissociation constant in acetonitrile.

<<Conjugate Base>>

The conjugate base is not particularly limited and may be appropriately selected depending on the intended purpose, as long as pKa of an acid that is a source of the conjugate base in acetonitrile is 10 or less. Examples of the conjugate base, other than the conjugate bases represented by General Formula (X) and General Formula (Y) below, include a conjugate base represented by General Formula (U) below, a conjugate base represented by General Formula (V) below, and a conjugate base represented by General Formula (W) below. Among the above-listed examples, a conjugate base represented by General Formula (X) below and a conjugate base represented by General Formula (Y) below are preferable because solubility of the ionic liquid to a solvent becomes high.

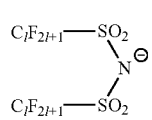

General Formula (X)

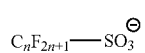

General Formula (Y)

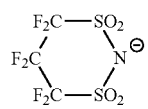

General Formula (U)

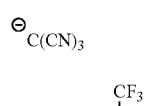

General Formula (V)

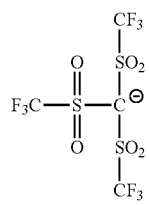

General Formula (W)

In General Formula (X), l is an integer of 1 or greater but 12 or less, and is preferably an integer of 1 or greater but 6 or less.

In General Formula (Y), n is an integer of 1 or greater but 12 or less, and is preferably an integer of 1 or greater but 6 or less.

As the acid that is a source of the conjugate base (HA), Bronsted acids regarded as super acid, such as bis((perfluoroalkyl)sulfonyl)imide $[C_lF_{2l+1}SO_2)_2NH]$ (pKa=0 to 0.3), perfluorocyclopropane sulfoimide (pKa=−0.8), perfluoroalkyl sulfonic acid ($C_mF_{2m+1}SO_3H$) (pKa=0.7), tris(perfluoroalkanesulfonyl)methide compounds $[(CF_3SO_2)_3CH]$ (pKa=−3.7), tricyanomethane (pKa=5.1), inorganic acids [e.g., nitric acid (pKa=9.4) and sulfuric acid (pKa=8.7)], tetrafluoroboric acid (pKa=1.8), and hexafluorophosphate, are preferable. The pKa of the above-listed acids are introduced, for example, in J. Org. Chem. Vol. 76, No. 2, p. 394.

<<Conjugate Acid>>

The conjugate acid is represented by General Formula (A) below.

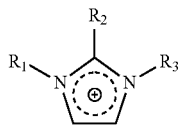

General Formula (A)

In General Formula (A), $R_1$, $R_2$, and $R_3$ are each independently a group including a hydrocarbon group, with the proviso that at least one of the hydrocarbon groups in $R_1$, $R_2$, and $R_3$ is a straight-chain hydrocarbon group having 6 or greater carbon atoms.

In the present specification, the "straight-chain hydrocarbon group having 6 or greater carbon atoms" may be a partially-fluorinated hydrocarbon group where part of hydrogen atoms bonded to carbon atoms is substituted with a fluorine atom. Examples of the partially-fluorinated hydrocarbon group include a fluorinated hydrocarbon group having 8 or greater carbon atoms including fluorinated hydrocarbon having 4 or greater carbon atoms.

The upper limit of the number of carbon atoms in the straight-chain hydrocarbon group having 6 or greater carbon atoms is not particularly limited and may be appropriately selected depending on the intended purpose. The upper limit of the number of carbon atoms is preferably 30 or less, more preferably 25 or less, and particularly preferably 20 or less in view of availability of raw materials. When the hydrocarbon group has a long chain, lubricity can be improved, with reducing a coefficient of friction.

The number of carbon atoms of at least one of the hydrocarbon groups in $R_1$, $R_2$, and $R_3$ is preferably 6 or greater but 15 or less, more preferably 8 or greater but 15 or less, and particularly preferably 10 or greater but 13 or less in view of solubility to fluorine-based solvents.

Since the solubility to solvents tends to be low when the number of carbon atoms is large, the number of carbon atoms of the hydrocarbon group is determined in view of both an effect of reducing a coefficient of friction, and solubility to solvents.

The hydrocarbon group may be a saturated hydrocarbon group, or an unsaturated hydrocarbon group partially including a double bond, or an unsaturated branched hydrocarbon group partially including a branched structure, as long as the hydrocarbon group is a straight-chain hydrocarbon group. Among the above-listed examples, an alkyl group, which is a saturated hydrocarbon group, is preferably in view of abrasion resistance. Moreover, the hydrocarbon group is preferably a straight-chain hydrocarbon group that does not include a branched structure even at part. Needless to say that the hydrocarbon group may be a hydrocarbon group partially including a branched structure.

<<Preferable Example of Ionic Liquid>>

The ionic liquid is preferably an ionic liquid represented by General Formula (1) below.

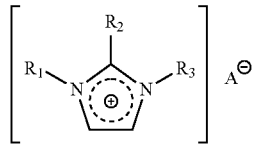

General Formula (1)

In General Formula (1), $A^-$ is a conjugate base, and $R_1$, $R_2$, and $R_3$ are each independently a group including a hydrocarbon group, with the proviso that at least one of the hydrocarbon groups in $R_1$, $R_2$, and $R_3$ is a straight-chain hydrocarbon group having 6 or greater carbon atoms.

The ionic liquid represented by General Formula (1) is preferably an ionic liquid represented by General Formula (1-1) below or an ionic liquid represented by General Formula (1-2).

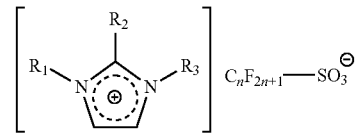

General Formula (1-1)

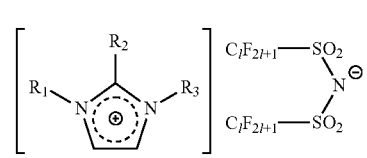

General Formula (1-2)

In General Formula (1-1), $R_1$, $R_2$, and $R_3$ are each independently a group including a hydrocarbon group, with the proviso that at least one of the hydrocarbon groups in $R_1$, $R_2$, and $R_3$ is a straight-chain hydrocarbon group having 6 or greater carbon atoms, and n is an integer of 1 or greater but 12 or less.

In General Formula (1-2), $R_1$, $R_2$, and $R_3$ are each independently a group including a hydrocarbon group, with the proviso that at least one of the hydrocarbon groups in $R_1$, $R_2$, and $R_3$ is a straight-chain hydrocarbon group having 6 or greater carbon atoms, and l is an integer of 1 or greater but 12 or less.

A synthesis method of the ionic liquid is not particularly limited and may be appropriately selected depending on the intended purpose. For example, various types of the ionic liquid can be synthesized with reference to the method disclosed in Examples below.

The ionic liquid of the present embodiment may be used alone as the lubricant, or the ionic liquid may be used in combination with a conventional lubricant. Examples of the lubricant used in combination include long-chain carboxylic acid, long-chain carboxylic acid ester, perfluoroalkyl carboxylic acid ester, perfluoroalkyl carboxylate, perfluoroalkyl perfluoroalkylcarboxylate, and a perfluoropolyether derivative.

Moreover, an extreme pressure agent may be used in combination at a blending ratio of about 30:70 to about 70:30 in a mass ratio in order to maintain a lubricating effect under severe conditions. The extreme pressure agent reacts with a surface of a metal with friction heat generated when the lubricant is partially in contact with the metal in a boundary lubrication region, and forms a coating film of a reaction product. As a result, friction and abrasion are prevented. As the extreme pressure agent, for example, any of a phosphorus-based extreme pressure agent, a sulfur-based extreme pressure agent, a halogen-based extreme pressure agent, an organic metal-based extreme pressure agent, or a complex extreme pressure agent can be used.

Moreover, an anti-rust agent may be optionally used in combination. The anti-rust agent may be any anti-rust agent typically used for this kind of magnetic recording media. Examples of the anti-rust agent include phenols, naphthols, quinones, heterocyclic compounds containing a nitrogen atom, heterocyclic compounds containing an oxygen atom, and heterocyclic compounds containing a sulfur atom. Moreover, the anti-rust agent may be mixed with the lubricant. Alternatively, the anti-rust agent and the lubricant may be deposited as two or more layers by forming a magnetic layer on a non-magnetic support, and applying an anti-rust agent layer on the upper part of the magnetic layer, followed by applying a lubricant layer.

As a solvent of the lubricant, for example, a single use or a combination of alcoholic solvents, such as isopropyl alcohol (IPA), and ethanol, can be used. For example, a mixture of a hydrocarbon-based solvent, such as normal-hexane, and a fluorine-based solvent can be used.

The solvent is preferably a fluorine-based solvent. Examples of the fluorine-based solvent include hydrofluoroethers [e.g., $C_3F_7OCH_3$, $C_4F_9OCH_3$, $C_4F_9OC_2H_5$, $C_2F_5CF(OCH_3)C_3F_7$, and $CF_3(CHF)_2CF_2CF_3$]. The fluorine-based solvent may be used as a mixture with alcohol, such as IPA, ethanol, and methanol.

The fluorine-based solvent may be a commercially available product. Examples of the commercially available product include: Novec™ 7000, 7100, 7200, 7300, and 71IPA available from 3M Company; and Vertrel XF, and X-P10 available from Du Pont-Mitsui Fluorochemicals Company, Ltd.

<2. Magnetic Recording Medium>

Next, a magnetic recording medium using the above-described lubricant is described. A magnetic recording medium described as one embodiment of the present invention includes at least a magnetic layer on a non-magnetic support, and the above-described lubricant is held on the magnetic layer.

The lubricant of the present embodiment can be applied for so-called a thin film-metal-type magnetic recording medium, in which a magnetic layer formed on a non-magnetic support by a method, such as vapor deposition and sputtering. Moreover, the lubricant can be also applied for a magnetic recording medium having a structure, in which a base layer is disposed between a non-magnetic support and a magnetic layer. Examples of such a magnetic recording medium include a magnetic disk, and a magnetic tape.

Figure 4:
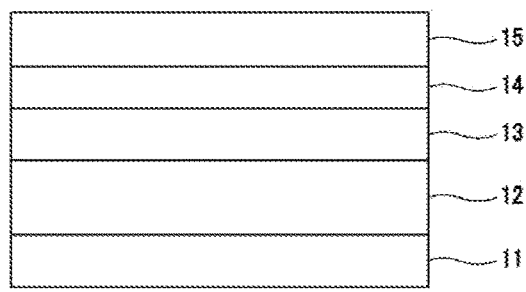
FIG. 4 is a cross-sectional view illustrating one example of a hard disk according to one embodiment of the present invention.

FIG. 4 is a cross-sectional view illustrating one example of a hard disk. The hard disk has a structure, in which a substrate 11, a base layer 12, a magnetic layer 13, a protective carbon layer 14, and a lubricant layer 15 are sequentially laminated.

Figure 5:
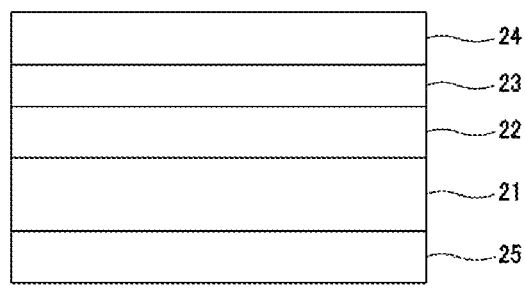
FIG. 5 is a cross-sectional view illustrating one example of a magnetic tape according to one embodiment of the present invention.

Moreover, FIG. 5 is a cross-sectional view illustrating one example of a magnetic tape. The magnetic tape has a structure, in which a back-coating layer 25, a substrate 21, a magnetic layer 22, a protective carbon layer 23, and a lubricant layer 24 are sequentially laminated.

In the magnetic disk illustrated in FIG. 4, each of the substrate 11 and the base layer 12 corresponds to the non-magnetic support. In the magnetic tape illustrated in FIG. 5, the substrate 21 corresponds to the non-magnetic support. In the case where a rigid substrate, such as an Al alloy plate, and a glass plate, is used as the non-magnetic support, a surface of the substrate may be made hard by forming an oxidized film, such as anodizing or a Ni—P coating on the surface of the substrate.

Each of the magnetic layers 13 and 22 is formed as a continuous film by a method, such as plating, sputtering, vacuum deposition, and plasma CVD. Examples of the magnetic layers 13 and 22 include: longitudinal magnetic recording metal magnetic films formed of metals (e.g., Fe, Co, and Ni), Co—Ni-based alloys, Co—Pt-based alloys, Co—Ni—Pt-based alloys, Fe—Co-based alloys, Fe—Ni-based alloys, Fe—Co—Ni-based alloys, Fe—Ni—B-based alloys, Fe—Co—B-based alloys, or Fe—Co—Ni—B-based alloys; and perpendicular magnetic recording metal magnetic thin films, such as Co—Cr-based alloy thin films, and Co—O-based thin films.

In the case where a longitudinal magnetic recording metal magnetic thin film is formed, particularly, a non-magnetic material, such as Bi, Sb, Pb, Sn, Ga, In, Ge, Si, and Tl, is formed as a base layer 12 on a non-magnetic support in advance, and a metal magnetic material is deposited through vapor deposition or sputtering in a perpendicular direction to diffuse the non-magnetic material into the magnetic metal thin film, to thereby improve a coercive force as well as eliminating orientation to assure in-plane isotopy.

Moreover, a hard protective layer 14 or 23, such as a carbon film, a diamond-formed carbon film, a chromium oxide film, and $SiO_2$ film, may be formed on a surface of the magnetic layer 13 or 22.

Examples of a method for applying the above-mentioned lubricant to such a metal thin film magnetic recording medium include a method for top-coating a surface of the magnetic layer 13 or 22, or a surface of the protective layer 14 or 23 with the lubricant, as illustrated in FIGS. 4 and 5. A coating amount of the lubricant is preferably from 0.1 $mg/m^2$ to 100 $mg/m^2$, more preferably from 0.5 $mg/m^2$ to 30 $mg/m^2$, and particularly preferably from 0.5 $mg/m^2$ to 20 $mg/m^2$.

As illustrated in FIG. 5, moreover, a metal thin film magnetic tape may optionally have a back-coating layer 25, other than a metal magnetic thin film, which is the magnetic layer 22.

The back-coating layer 25 is formed by adding a carbon-based powder for imparting conductivity, or an inorganic pigment for controlling a surface roughness to a resin binder, and applying the resin binder mixture. In the present embodiment, the above-described lubricant may be internally added to the back-coating layer 25, or applied to the back-coating layer 25 as top coating. Moreover, the above-described lubricant may be internally added to both the magnetic layer 22 and the back-coating layer 25, or applied to both the magnetic layer 22 and the back-coating layer 25 as top coating.

As another embodiment, moreover, the lubricant can be applied for a so-called coating-type magnetic recording medium, in which a magnetic coating film is formed as a magnetic layer by applying a magnetic coating material onto a surface of a non-magnetic support. In the coating-type magnetic recording medium, the non-magnetic support, a magnetic powder constituting the magnetic coating film, and the resin binder for use can be selected from any of those known in the art.

Examples of the non-magnetic support include: polymer substrates formed of polymer materials, such as polyesters, polyolefins, cellulose derivatives, vinyl-based resins, polyimides, polyamides, and polycarbonate; metal substrates formed of aluminium alloys, or titanium alloys; ceramic substrates formed of alumina glass; and glass substrates. Moreover, a shape of the non-magnetic support is not particularly limited, and may be any form, such as a tape, a sheet, and a drum. Furthermore, the non-magnetic support may be subjected to a surface treatment to form fine irregularities in order to control surface properties of the non-magnetic support.

Examples of the magnetic powder include: ferromagnetic iron oxide-based particles, such as $\gamma$-$Fe_2O_3$, cobalt-coated $\gamma$-$Fe_2O_3$; ferromagnetic chromium dioxide; ferromagnetic metal-based particles formed of a metal, such as Fe, Co, and Ni, or an alloy containing any of the above-listed metals; and hexagonal ferrite particles in the form of hexagonal plates.

Examples of the resin binder include: polymers, such as vinyl chloride, vinyl acetate, vinyl alcohol, vinylidene chloride, acrylic acid ester, methacrylic acid ester, styrene, butadiene, and acrylonitrile; copolymers combining two or more selected from the above-listed polymers; polyurethane resins; polyester resins; and epoxy resins. In order to improve dispersibility of the magnetic powder, a hydrophilic polar group, such as a carboxylic acid group, a carboxyl group, and a phosphoric acid group, may be introduced into any of the above-listed binders.

Other than the magnetic powder and the resin binder, additives, such as a dispersing agent, an abrasive, an anti-static agent, and an anti-rust agent, may be added to the magnetic coating film.

As a method for retaining the above-described lubricant in the coating-type magnetic recording medium, there are a method where the lubricant is internally added to the magnetic layer constituting the magnetic coating film formed on the non-magnetic support, a method where the lubricant is applied on a surface of the magnetic layer as top coating, and a combination of the above-listed methods. In the case where the lubricant is internally added into the magnetic coating film, the lubricant is added in an amount of from 0.2 parts by mass to 20 parts by mass relative to 100 parts by mass of the resin binder.

In the case where a surface of the magnetic layer is top-coated with the lubricant, moreover, a coating amount of the lubricant is preferably from 0.1 mg/m$^2$ to 100 mg/m$^2$, and more preferably from 0.5 mg/m$^2$ to 20 mg/m$^2$. As a deposition method in the case where the lubricant is applied as top coating, the ionic liquid is dissolved in a solvent, and the obtained solution may be applied or sprayed, or a magnetic recording medium may be dipped in the solution.

The magnetic recording medium, to which the lubricant of the present embodiment is applied, exhibits excellent running performances, abrasion resistance, and durability because of a lubricating effect, and can further improve thermal stability.

EXAMPLES

<3. Examples>

Specific examples of the present invention are explained below. In the examples, ionic liquids were synthesized, and lubricants including the ionic liquids were produced. Then, solubility of the ionic liquids to Vertrel [$CF_3(CHF)_2CF_2CF_3$], which was a fluorine-based solvent, and to n-hexane, which was a hydrocarbon-based solvent, were determined. Then, the lubricant solutions were applied surfaces of the magnetic disks and magnetic tapes and durability of each disk and durability of each tape were evaluated. Production of a magnetic disk, a durability test of the disk, production of a magnetic tape, and a durability test of the tape were performed in the following manner. Note that, the present invention is not limited to these examples.

<Production of Magnetic Disk>

A magnetic thin film was formed on a glass substrate to produce a magnetic disk as illustrated in FIG. 4, for example, according to International Patent Publication No. WO2005/068589. Specifically, a chemically reinforced glass disk, which was formed of aluminium silicate glass and had an outer diameter of 65 mm, an inner diameter of 20 mm, and a disk thickness of 0.635 mm, was prepared, and a surface of the glass disk was polished so that Rmax of the surface was to be 4.8 nm, and Ra of the surface was to be 0.43 nm. The glass substrate was subjected to ultrasonic cleaning for 5 minutes each in pure water and in isopropyl alcohol (IPA) having the purity of 99.9% or greater, and the washed glass substrate was left to stand in saturated IPA steam for 1.5 minutes, followed by drying. The resultant glass substrate was provided as a substrate 11.

On the substrate 11, a NiAl alloy (Ni: 50 mol %, Al: 50 mol %) thin film in the thickness of 30 nm as a seed layer, a CrMo alloy (Cr: 80 mol %, Mo: 20 mol %) thin film in the thickness of 8 nm as a base layer 12, and a CoCrPtB alloy (Co: 62 mol %, Cr: 20 mol %, Pt: 12 mol %, B: 6 mol %) thin film in the thickness of 15 nm as a magnetic layer 13 were sequentially formed by DC magnetron sputtering.

Subsequently, a 5 nm-thick protective carbon layer 14 formed of amorphous diamond-like carbon was formed by plasma CVD, and the resultant disk sample was subjected to ultrasonic cleaning for 10 minutes in isopropyl alcohol (IPA) having the purity of 99.9% or greater inside a cleaner to remove impurities on a surface of the disk, followed by drying. Thereafter, a n-hexane/ethanol mixed solution of an ionic liquid was applied on a surface of the disk by dip coating in the environment of 25° C. and 50% in relative humidity (RH), to form about 1 nm of a lubricant layer 15.

<Measurement of Thermal Stability>

In the TG/DTA measurement, the measurement was performed by means of EXSTAR6000 available from Seiko Instruments Inc. at a temperature range of from 30° C. to 600° C. at a heating rate of 10° C./min with introducing air at a flow rate of 200 mL/min.

<Disk Durability Test>

A CSS durability test was performed by means of a commercially available strain-gauge-type disk friction-abrasion tester in the following manner. A hard disk was mounted on a rotatable spindle with tightening torque of 14.7 Ncm. Thereafter, a head slider was attached on the hard disk in a manner that a center of an air bearing surface at the inner circumference side of the head slider relative to the hard disk was 17.5 mm from a center of the hard disk. The head used for the measurement was an IBM3370-type inline head, a material of the slider was $Al_2O_3$—TiC, and the head load was 63.7 mN. In the test, the maximum value of friction force was monitored per CSS (contact, start, and stop) in the environment of 100 in cleanliness, 25° C., and 60% RH. The number of times when a coefficient of friction was greater than 1.0 was determined as a result of the CSS durability test. When a result of the CSS durability test was greater than 50,000, the result was represented as ">50,000." Moreover, a CSS durability test was similarly performed after performing a heating test for 3 minutes at a temperature of 200° C., in order to study heat resistance.

<Production of Magnetic Tape>

A magnetic tape having a cross-sectional structure as illustrated in FIG. 5 was produced. First, Co was deposited on a substrate 21 formed of a 5 μm-thick MICTRON (aromatic polyamide) film available from TORAY INDUSTRIES, INC. by oblique deposition to form a magnetic layer 22 formed of a ferromagnetic metal thin film having a film thickness 100 nm. Next, a protective carbon layer 23 formed of a 10 nm-thick diamond-like carbon was formed on a surface of the ferromagnetic metal thin film by plasma CVD, followed by cutting the resultant into a strip having a width of 6 mm. An ionic liquid dissolved in IPA was applied onto the protective carbon layer 23 in a manner that a film thickness of the ionic liquid solution was about 1 nm. In this manner, a lubricant layer 24 is formed on the magnetic layer to thereby produce a sample tape.

<Tape Durability Test>

Each sample tape was subjected to a measurement of still durability in an environment having a temperature of −5° C. and in an environment having a temperature of 40° C. and 30% RH, and measurements of a coefficient of friction and shuttle durability in an environment having a temperature of −5° C. and in an environment having a temperature of 40° C. and 90% RH. The still durability was evaluated by a decay time of an output in a paused state decayed by −3 dB. The shuttle resistant was evaluated by the number of shuttles taken until an output was reduced by 3 dB when repeated shuttle run was performed for 2 minutes per time. Moreover, a durability test was similarly performed after performing a heating test for 10 minutes at a temperature of 100° C., in order to study heat resistance.

In the present specification, the measurement of FTIR was performed by means of FT/IR-460 available from JASCO Corporation according to a transmission method using KBr plates or KBr pellets. The resolution of the measurement was 4 cm$^{-1}$.

The $^1$H-NMR and $^{13}$C-NMR spectra were measured by means of Varian Mercury Plus 300 nuclear magnetic resonance spectrometer (available from Varian, Inc.). A chemical shift of $^1$HNMR was represented with ppm comparing with an internal standard (TMS or deuterated solvent peak at 0 ppm). Splitting patterns were presented by denoting a singlet as s, a doublet as d, a triplet as t, a quartet as q, a quintet as quin, a multiplet as m, and a broad peak as br.

Example 1A

Synthesis of Nonafluorobutanesulfonic acid-1,3-didodecyl-2-undecylimidazolium

A synthesis of nonafluorobutanesulfonic acid-1,3-didodecyl-2-undecylimidazolium was performed according to the following scheme.

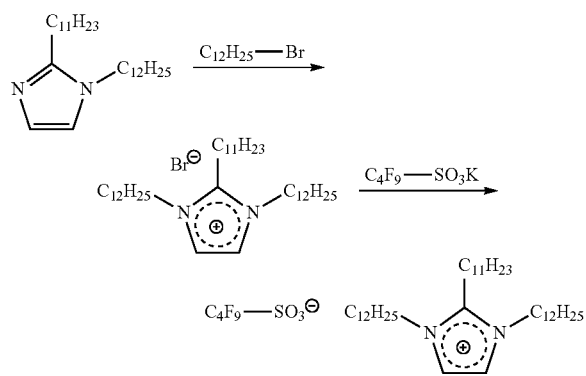

A flask was charged with 17.76 g of 2-undecylimidazole, 20.00 g of dodecyl bromide, 7.75 g of potassium hydroxide, and the mixture was heated in toluene under reflux for 8.0 hours. After returning the temperature to room temperature, the solvent was removed. The resultant was purified by silica gel chromatography using a mixed solvent of n-hexane and ethyl acetate [n-hexane:ethyl acetate (volume ratio)=9:1] as an eluent, to obtain 27.35 g of 1-dodecyl-2-undecylimidazole which was a colorless liquid. A purity of 27.35 g of the 1-dodecyl-2-undecylimidazole as measured by gas chromatography was 98.8% or greater. The yield was 87.7%.

A flask was charged with 6.83 g of 1-dodecyl-2-undecylimidazole and 4.59 g of dodecyl bromide, and the resultant mixture was heated at 120° C. for 4.0 hours. The temperature was then returned to room temperature to crystallize a reaction product, and the crystallized product was recrystallized with ethyl acetate to thereby obtain 10.61 g of 1,3-didodecyl-2-undecylimidazoliumbromide, which was colorless crystals. The yield was 94.8%.

The FTIR absorbance peaks of the product and the assignments are presented below.

The bending vibrations of $CH_2$ were observed at 1,468 cm$^{-1}$, the symmetric stretching vibrations of C=N were observed at 1,575 cm$^{-1}$, symmetric stretching vibrations of $CH_2$ were observed at 2,850 cm$^{-1}$, asymmetric stretching vibrations of $CH_2$ were observed at 2,918 cm$^{-1}$, and CH stretching vibrations of imidazole rings were observed at 2,956 cm$^{-1}$, 3,026 cm$^{-1}$, and 3,070 cm$^{-1}$.

Moreover, peaks of the protons ($^1$H)NMR and carbons ($^{13}$C)NMR in deuterated chloroform are presented below.

$^1$H-NMR(CDCl$_3$, δ ppm): 0.841 (t/J=6.8 Hz, 9H), 1.140-1.440 (m, 52H), 1.586 (quint/J=7.8 Hz, 2H), 1.837 (quint/J=7.2 Hz, 4H), 3.014 (t/J=8.0 Hz, 2H), 4.181 (t/J=7.8 Hz, 4H), 7.708 (s, 2H)

$^{13}$C-NMR (CDCl$_3$, δ ppm): 14.051, 22.618, 23.940, 26.422, 27.869, 29.048, 29.278, 29.355, 29.479, 29.556, 30.217, 31.846, 48.673, 121.866, 145.804

The product was determined as 1,3-didodecyl-2-undecylimidazoliumbromide from the spectra above.

In ethanol, 3.87 g of 1,3-didodecyl-2-undecylimidazoliumbromide was dissolved. To the resultant solution, a solution prepared by dissolving 2.08 g of potassium nonafluorobutanesulfonate in pure water upon heating was added, and the resultant mixture was heated under reflux for 1 hour. After cooling the resultant, the solvent was removed, and the residues were extracted with dichloromethane. The obtained organic layer was sufficiently washed with pure water until a result of the AgNO$_3$ test became negative. After drying the resultant with anhydrous sodium sulfate, the solvent was removed to thereby obtain 4.81 g of nonafluorobutanesulfonic acid-1,3-didodecyl-2-undecylimidazolium, which was colorless crystals. The yield was 92.6%.

The FTIR absorbance peaks of the product and the assignments are presented below.

The symmetric stretching vibrations of $SO_2$ bonds were observed at 1,054 cm$^{-1}$, symmetric stretching vibrations of $CF_2$ were observed at 1,134 cm$^{-1}$ and 1,263 cm$^{-1}$, the asymmetric stretching vibrations of $SO_2$ bonds were observed at 1,352 cm$^{-1}$, the bending vibrations of $CH_2$ bonds were observed at 1,466 cm$^{-1}$, symmetric stretching vibrations of C=N bonds were observed at 1,524 cm$^{-1}$, symmetric stretching vibrations of $CH_2$ bonds were observed at 2,856 cm$^{-1}$, the asymmetric stretching vibrations of $CH_2$ bonds were observed at 2,926 cm$^{-1}$, and the stretching vibrations of CH bonds of imidazole rings were observed at 3,129 cm$^{-1}$.

Moreover, peaks of the protons ($^1$H)NMR and carbons ($^{13}$C)NMR in deuterated chloroform are presented below.

$^1$H-NMR(CDCl$_3$, δ ppm): 0.850 (t/J=6.8 Hz, 9H), 1.140-1.440 (m, 52H), 1.577 (quint/J=7.8 Hz, 2H), 1.810 (quint/J=7.3 Hz, 4H), 2.947 (t/J=8.0 Hz, 2H), 4.064 (t/J=7.6 Hz, 4H), 7.390 (s, 2H)

$^{13}$C-NMR (CDCl$_3$, δ ppm): 14.070, 22.637, 23.471, 26.403, 27.726, 29.010, 29.297, 29.345, 29.479, 29.565, 30.016, 31.856, 48.491, 121.435, 146.024

The product was determined as nonafluorobutanesulfonic acid-1,3-didodecyl-2-undecylimidazolium from the spectra above.

Note that, a pKa of an acid (nonafluorobutanesulfonic acid) that was a source of the conjugate base in the nonafluorobutanesulfonic acid-1,3-didodecyl-2-undecylimidazolium was 0.7 in acetonitrile.

Example 2A

Synthesis of bis(nonafluorobutanesulfonyl)imide-1,3-didodecyl-2-undecylimidazolium A synthesis of bis(nonafluorobutanesulfonyl)imide-1,3-didodecyl-2-undecylimidazolium was performed according to the following scheme.

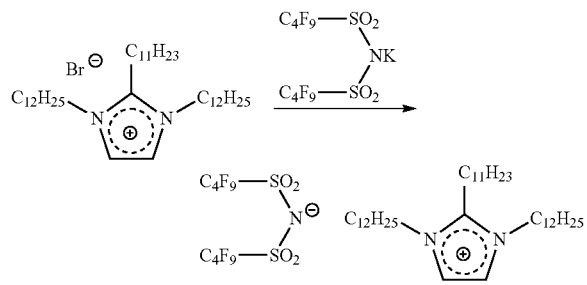

In ethanol, 3.32 g of 1,3-didodecyl-2-undecylimidazoliumbromide synthesized in the same manner as in Example 1A was dissolved. To the resultant solution, a solution prepared by dissolving 3.20 g of bis(nonafluorobutanesulfonyl)imide potassium salt in a mixed solvent of pure water and ethanol upon heating was added, and the resultant mixture was heated under reflux for 1 hour. The solvent was removed from the solution, and the residues together with precipitates were extracted with dichloromethane. The obtained organic layer was sufficiently washed with pure water until a result of the $AgNO_3$ test became negative. After drying the resultant with anhydrous sodium sulfate, the solvent was removed to thereby obtain 5.52 g of bis(nonafluorobutanesulfonyl)imide-1,3-didodecyl-2-undecylimidazolium, which was a colorless liquid. The yield was 93.3%.

The FTIR absorbance peaks of the product and the assignments are presented below.

The asymmetric stretching vibrations of SNS bonds were observed at 1,076 $cm^{-1}$, the symmetric stretching vibrations of $CF_2$ were observed at 1,139 $cm^{-1}$, 1,169 $cm^{-1}$, and 1,236 $cm^{-1}$, the asymmetric stretching vibrations of $SO_2$ bonds were observed at 1,354 $cm^{-1}$, the bending vibrations of $CH_2$ bonds were observed at 1,467 $cm^{-1}$, the symmetric stretching vibrations of C=N bonds were observed at 1,523 $cm^{-1}$, the symmetric stretching vibrations of $CH_2$ bonds were observed at 2,857 $cm^{-1}$, the asymmetric stretching vibrations of $CH_2$ bonds were observed at 2,927 $cm^{-1}$, and the stretching vibrations of CH bonds of imidazole rings were observed at 3,141 $cm^{-1}$.

Moreover, peaks of the protons ($^1$H)NMR and carbons ($^{13}$C)NMR in deuterated chloroform are presented below.

$^1$H-NMR ($CDCl_3$, δ ppm): 0.852 (t/J=7.0 Hz, 9H), 1.140-1.440 (m, 52H), 1.564 (quint/J=8.0 Hz, 2H), 1.801 (quint/J=7.3 Hz, 4H), 2.902 (t/J=8.2 Hz, 2H), 4.014 (t/J=7.8 Hz, 4H), 7.247 (s, 2H)

$^{13}$C-NMR ($CDCl_3$, δ ppm): 14.061, 22.647, 23.327, 26.374, 27.611, 28.952, 29.307, 29.470, 29.565, 29.910, 31.875, 48.491, 121.243, 146.005

The product was determined as bis(nonafluorobutanesulfonyl)imide-1,3-didodecyl-2-undecylimidazolium from the spectra above.

Note that, a pKa of an acid [bis(nonafluorobutanesulfonyl)imide] that was a source of the conjugate base in the bis(nonafluorobutanesulfonyl)imide-1,3-didodecyl-2-undecylimidazolium was 0.0 in acetonitrile.

Example 3A

Synthesis of Nonafluorobutanesulfonic acid-1,3-dioctadecyl-2-heptadecylimidazolium A synthesis of nonafluorobutanesulfonic acid-1,3-dioctadecyl-2-heptadecylimidazolium was performed according to the following scheme.

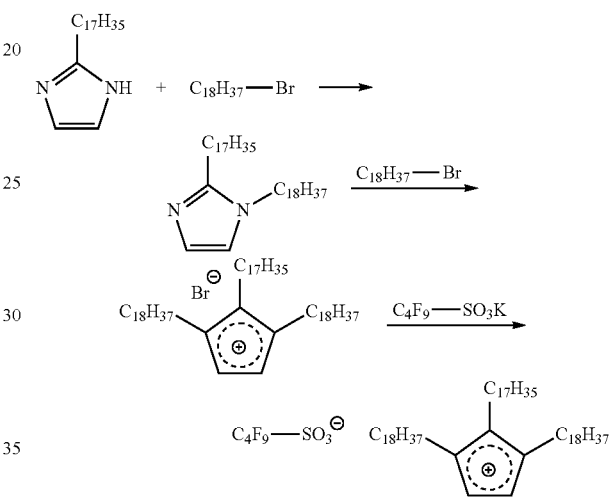

A raw material, 2-heptadecylimidazole, was purchased from SHIKOKU CHEMICALS CORPORATION, and was used after recrystallizing with ethanol. Since thermal stability improved by improving the purity from 93% to 98.5% through recrystallization, the purified product through recrystallization was used as the 2-heptadecyl imidazole used below as a synthesis raw material.

A flask was charged with 15.34 g of the 2-heptadecyl imidazole, 17.62 g of octadecyl bromide, and 4.86 g of potassium hydroxide, and the resultant mixture was heated in toluene under reflux for 11.0 hours. After returning to the room temperature, the solvent was removed from the resultant, and purification was performed through silica gel chromatography using a mixed solvent of n-hexane and ethyl acetate [n-hexane:ethyl acetate (volume ratio)=9:1] as an eluent. The purity of 27.81 g of 1-octadecyl-2-heptadecylimidazole, which was colorless crystals, as determined by gas chromatography was 99.5% or greater. The yield was 99.4%.

A flask was charged with 5.69 g of 1-octadecyl-2-heptadecylimidazole and 3.81 g of octadecyl bromide, and the resultant mixture was heated at 120° C. for 4.0 hours. After returning the resultant to the room temperature to generate a crystallized product, the product was recrystallized with ethyl acetate to thereby obtain 9.35 g of 1,3-dioctadecyl-2-heptadecylimidazoliumbromide, which was colorless crystals. The yield was 98.2%.

The FTIR absorbance peaks of the product and the assignments are presented below.

The bending vibrations of CH$_2$ were observed at 1,468 cm$^{-1}$, the symmetric stretching vibrations of C=N were observed at 1,576 cm$^{-1}$, the symmetric stretching vibrations of CH$_2$ were observed at 2,850 cm$^{-1}$, the asymmetric stretching vibrations of CH$_2$ were observed at 2,918 cm$^{-1}$, and stretching vibrations of CH of imidazole rings were observed at 3,023 cm$^{-1}$ and 3,069 cm$^{-1}$.

Moreover, peaks of the protons ($^1$H)NMR and carbons ($^{13}$C)NMR in deuterated chloroform are presented below.

$^1$H-NMR(CDCl$_3$, δ ppm): 0.848 (t/J=6.8 Hz, 9H), 1.140-1.450 (m, 88H), 1.590 (quint/J=8.0 Hz, 2H), 1.843 (quint/J=8.4 Hz, 4H), 3.016 (t/J=8.4 Hz, 2H), 4.178 (t/J=7.6 Hz, 4H), 7.688 (s, 2H)

$^{13}$C-NMR (CDCl$_3$, δ ppm): 14.070, 22.647, 23.988, 26.441, 27.869, 29.058, 29.326, 29.374, 29.508, 29.633, 29.680, 30.208, 31.894, 48.693, 121.828, 145.862

The product was determined as 1,3-dioctadecyl-2-heptadecylimidazoliumbromide from the spectra above.

In ethanol, 3.56 g of the 1,3-dioctadecyl-2-heptadecylimidazoliumbromide was dissolved. To the resultant solution, a solution obtained by dissolving 1.36 g of potassium nonafluorobutanesulfonate in an ethanol aqueous solution upon heating was added, and the resultant mixture was heated under reflux for 1 hour. After cooling, the precipitates were extracted with dichloromethane, and the obtained organic layer was sufficiently washed with pure water until a result of the AgNO$_3$ test became negative. After drying the resultant with anhydrous sodium sulfate, the solvent was removed to thereby obtain 4.10 g of nonafluorobutanesulfonic acid-1,3-octadodecyl-2-heptadecylimidazolium, which was colorless crystals. The yield was 92.4%.

The FTIR absorbance peaks of the product and the assignments are presented below.

The symmetric stretching vibrations of SO$_2$ bonds were observed at 1,054 cm$^{-1}$, the symmetric stretching vibrations of CF$_2$ at 1,133 cm$^{-1}$ and 1,264 cm$^{-1}$, the asymmetric stretching vibrations of SO$_2$ bonds were observed at 1,352 cm$^{-1}$, the bending vibrations of CH$_2$ bonds were observed at 1,468 cm$^{-1}$, the symmetric stretching vibrations of C=N bonds were observed at 1,524 cm$^{-1}$, the symmetric stretching vibrations of CH$_2$ bonds were observed at 2,851 cm$^{-1}$, and the asymmetric stretching vibrations of CH$_2$ bonds were observed at 2,919 cm$^{-1}$.

Moreover, peaks of the protons ($^1$H)NMR and carbons ($^{13}$C)NMR in deuterated chloroform are presented below.

$^1$H-NMR (CDCl$_3$, δ ppm): 0.856 (t/J=6.8 Hz, 9H), 1.140-1.450 (m, 88H), 1.530-1.630 (m, 2H), 1.807 (quint/J=7.2 Hz, 4H), 2.906 (t/J=8.4 Hz, 2H), 4.018 (t/J=7.6 Hz, 4H), 7.247 (s, 2H)

$^{13}$C-NMR (CDCl$_3$, δ ppm): 14.099, 22.675, 23.375, 26.394, 27.620, 28.971, 29.355, 29.489, 29.594, 29.661, 29.700, 29.910, 31.913, 48.511, 121.234, 146.024

The product was determined as nonafluorobutanesulfonic acid-1,3-dioctadecyl-2-heptadecylimidazolium from the spectra above.

Note that, a pKa of an acid (nonafluorobutanesulfonic acid) that was a source of the conjugate base in the nonafluorobutanesulfonic acid-1,3-dioctadecyl-2-heptadecylimidazolium was 0.7 in acetonitrile.

Example 4A

Synthesis of bis(nonafluorobutanesulfonyl)imide-1,3-dioctadecyl-2-heptadecylimidazolium A synthesis of bis(nonafluorobutanesulfonyl)imide-1,3-dioctadecyl-2-heptadecylimidazolium was performed according to the following scheme.

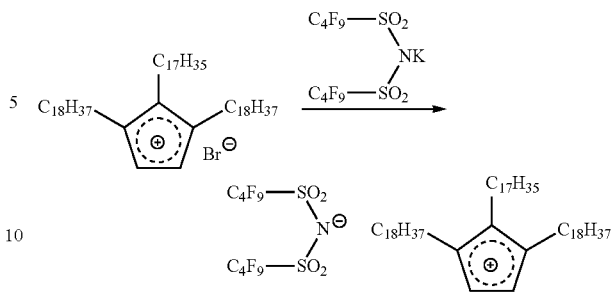

In ethanol, 3.82 gg of the 1,3-dioctadecyl-2-heptadecylimidazoliumbromide synthesized in Example 3A was dissolved. To the resultant solution, a solution prepared by dissolving 2.66 g of bis(nonafluorobutanesulfonyl)imide potassium salt in an ethanol aqueous solution upon heating was added, and the resultant mixture was heated under reflux for 1 hour. After cooling the resultant, the precipitates were extracted with dichloromethane, and the obtained organic layer was sufficiently washed with pure water until a result of the AgNO$_3$ test became negative. After drying the resultant with anhydrous sodium sulfate, the solvent was removed to thereby obtain 5.41 g of bis(nonafluorobutanesulfonyl)imide-1,3-dioctadecyl-2-heptadecylimidazolium, which was colorless crystals. The yield was 90.7%.

The FTIR absorbance peaks of the product and the assignments are presented below.

The asymmetric stretching vibrations of SNS bonds were observed at 1,075 cm$^{-1}$, the symmetric stretching vibrations of CF$_2$ were observed at 1,139 cm$^{-1}$, 1,169 cm$^{-1}$, and 1,235 cm$^{-1}$, the asymmetric stretching vibrations of SO$_2$ bonds were observed at 1,354 cm$^{-1}$, the bending vibrations of CH$_2$ were observed at 1,467 cm$^{-1}$, the stretching vibrations of C=N were observed at 1,523 cm$^{-1}$, the symmetric stretching vibrations of CH$_2$ were observed at 2,851 cm$^{-1}$, and the asymmetric stretching vibrations of CH$_2$ were observed at 2,920 cm$^{-1}$.

Moreover, peaks of the protons ($^1$H)NMR and carbons ($^{13}$C)NMR in deuterated chloroform are presented below.

$^1$H-NMR(CDCl$_3$, δ ppm): 0.854 (t/J=7.0 Hz, 9H), 1.140-1.440 (m, 88H), 1.580 (quint/J=7.2 Hz, 2H), 1.817 (quint/J=7.0 Hz, 4H), 2.955 (t/J=8.0 Hz, 2H), 4.069 (t/J=7.8 Hz, 4H), 7.383 (s, 2H)

$^{13}$C-NMR (CDCl$_3$, δ ppm): 14.099, 22.675, 23.548, 26.432, 27.735, 29.019, 29.345, 29.508, 29.604, 29.652, 29.690, 30.006, 31.904, 48.520, 121.406, 146.092

The product was determined as bis(nonafluorobutanesulfonyl)imide-1,3-dioctadecyl-2-heptadecylimidazolium from the spectra above.

Note that, a pKa of an acid [bis(nonafluorobutanesulfonyl)imide] that was a source of the conjugate base in the bis(nonafluorobutanesulfonyl)imide-1,3-dioctadecyl-2-heptadecylimidazolium was 0.0 in acetonitrile.

Comparative Example 1A

Synthesis of Nonafluorobutanesulfonic acid-1-octadecylimidazolium

A nonafluorobutanesulfonic acid-1-octadecylimidazolium was performed according to the following scheme.

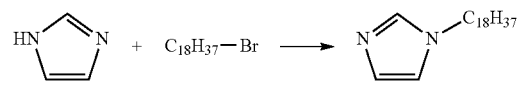

-continued

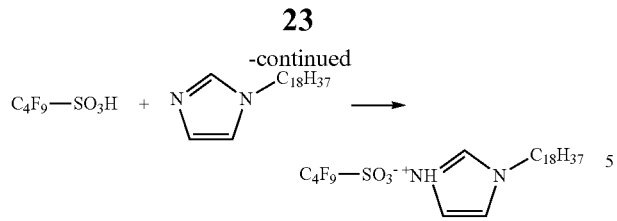

1-Octadecylimidazole was synthesized by the following method.

In 100 mL of acetonitrile, 3 g of imidazole was dissolved. To the resultant solution, 14.9 g of octadecyl bromide and 2.51 g of potassium hydroxide were added, and the mixture was heated under reflux with stirring for 4 hours. After removing the solvent from the resultant, extraction was performed with dichloromethane, followed by performing purification by column chromatography. As a result of the analysis of gas chromatography, the purity was 98.5% or higher.

Subsequently, 3.27 g of the synthesized 1-octadecylimidazole was dissolved in 50 mL of ethanol. To the resultant solution, an ethanol solution including 3.05 g of nonafluorobutanesulfonic acid was gradually added by dripping. After the completion of the dripping, the resultant was stirred for 30 minutes, followed by heating under reflux for 1 hour. After removing the solvent from the resultant, recrystallization was performed using a mixed solvent of ethanol and n-hexane to thereby obtain colorless nonafluorobutanesulfonic acid-1-octadecylimidazolium. The yield was 95%.

The assignments of the FTIR spectrum are presented below.

The symmetric stretching vibrations of $SO_2$ were observed at 1,134 $cm^{-1}$, the asymmetric stretching vibrations of $SO_2$ bonds were observed at 1,355 $cm^{-1}$, the symmetric stretching vibrations of $CF_2$ were observed at 1,246 $cm^{-1}$, the bending vibrations of CH bonds were observed at 1,470 $cm^{-1}$, the symmetric stretching vibrations of $CH_2$ were observed at 2,852 $cm^{-1}$, the asymmetric stretching vibrations of $CH_2$ were observed at 2,920 $cm^{-1}$, and the stretching vibrations of CH bonds of imidazole rings were observed at 3,158 $cm^{-1}$.

Moreover, peaks of the protons ($^1H$)NMR and carbons ($^{13}C$)NMR in deuterated chloroform are presented below.

$^1$H-NMR (CDCl$_3$, δ ppm): 0.847 (t, 3H, J=7.2 Hz), 1.222-1.282 (m, 30H), 1.790-1.890 (m, 2H), 4.181 (t/J=7.2 Hz, 2H), 7.189 (dd/J=1.8 Hz, 3.8 Hz, 111), 7.444 (dd/J=1.8 Hz, 3.8 Hz, 111), 8.866 (dd/J=1.8 Hz, 3.8 Hz, 111), 13.200 (brs, 1H)

$^{13}$C-NMR (CDCl$_3$, δ ppm): 14.055, 22.648, 26.113, 28.875, 29.272, 29.318, 29.440, 30.142, 31.882, 49.847, 122.500, 122.851, 135.015

It was confirmed from above that nonafluorobutanesulfonic acid-1-octadecylimidazolium was synthesized.

Comparative Example 2A

Synthesis of hexafluorocyclopropane-1,3-bis(sulfonyl)imide-1-butyl-3-n-octadecylimidazolium For comparison, a synthesis of hexafluorocyclopropane-1,3-bis(sulfonyl)imide-1-butyl-3-n-octadecylimidazolium was performed according to the following scheme.

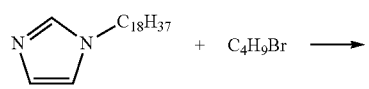

-continued

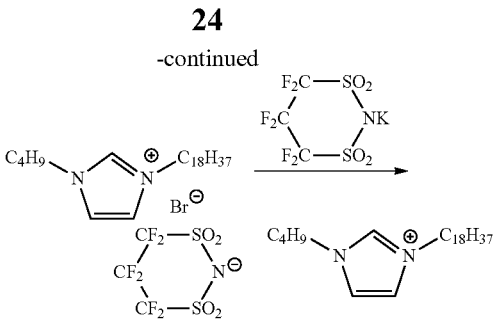

In acetonitrile, 10.7 g of the 1-octadecylimidazole synthesized in Comparative Example 1 and 6.03 g of bromobutane were dissolved, and the resultant mixture was heated under reflux for 5 hours. After removing the solvent from the resultant, recrystallization was performed using a mixed solvent of n-hexane and ethanol to thereby obtain 1-butyl-3-octadecylimidazoliumbromide. In ethanol, 4.57 g of the 1-butyl-3-octadecylimidazoliumbromide was dissolved. To the resultant solution, an ethanol solution, in which 3.31 g of potassium hexafluorocyclopropane-1,3-bis(sulfonyl)imide had been dissolved, was added. Upon stirring of the resultant solution, sedimentation of a colorless substance occurred. The solution was heated under reflux for 1 hour. After cooling the resultant, the solvent was removed. To the resultant, dichloromethane was added, and the soluble component was separated through filtration. The resultant organic layer was washed with pure water until the result of the AgNO$_3$ test became negative. The resultant was dried, and recrystallized using a mixed solvent of n-hexane and ethanol, to thereby obtain 6.00 g of hexafluorocyclopropane-1,3-bis(sulfonyl)imide-1-butyl-3-n-octadecylimidazolium, which was colorless crystals. The yield was 90%.

The FTIR absorbance peaks of the product and the assignments are presented below.

The symmetric stretching vibrations of SNS were observed at 1,091 $cm^{-1}$, the symmetric stretching vibrations of $CF_2$ were observed at 1,161 $cm^{-1}$, the asymmetric stretching vibrations of $SO_2$ bonds were observed at 1,356 $cm^{-1}$, the bending vibrations of CH bonds were observed at 1,470 $cm^{-1}$, the stretching vibrations unique to imidazole were observed at 1,560 $cm^{-1}$, the symmetric stretching vibrations of $CH_2$ were observed at 2,850 $cm^{-1}$, and the asymmetric stretching vibrations of $CH_2$ were observed at 2,919 $cm^{-1}$.

Moreover, peaks of the protons ($^1H$)NMR and carbons ($^{13}C$)NMR in deuterated chloroform are presented below.

$^1$H-NMR (CDCl$_3$, δ ppm): 0.850 (t, 3H, J=7.2 Hz), 0.941 (t, 3H, J=7.2 Hz), 1.170-1.410 (m, 32H), 1.835 (quint, J=7.2 Hz, 4H), 4.160 (m, 411), 7.267 (d, 1H, J=2.1 Hz), 7.294 (d, 1H, J=2.1 Hz), 8.749 (s, 1H)

$^{13}$C-NMR (CDCl$_3$, δ ppm): 13.254, 14.085, 19.351, 22.663, 26.113, 28.853, 29.303, 29.333, 29.448, 29.570, 29.631, 29.677, 30.127, 31.898, 32.004, 49.977, 50.244, 122.179, 122.263, 135.473

The product was determined as hexafluorocyclopropane-1,3-bis(sulfonyl)imide-1-butyl-3-n-octadecylimidazolium from the spectra above.

Note that, a pKa of an acid [hexafluorocyclopropane-1,3-bis(sulfonyl)imide] that was a base of the conjugate base in the hexafluorocyclopropane-1,3-bis(sulfonyl)imide-1-butyl-3-n-octadecylimidazolium was −0.8 in acetonitrile.

Comparative Example 3A

Synthesis of Nonafluorobutanesulfonic acid-2-heptadecylimidazole Salt

A synthesis of nonafluorobutanesulfonic acid-2-heptadecylimidazole salt was performed according to the following scheme.

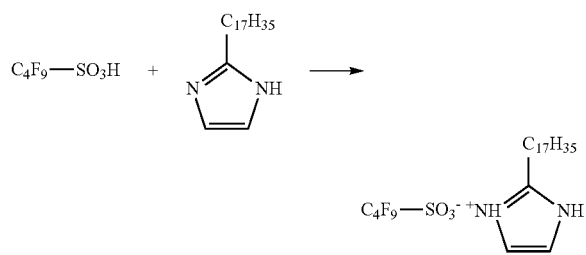

In 100 mL of ethanol, 5.10 g of 2-heptadecylimidazole was dissolved. To the resultant solution, 5.00 g of nonafluorobutanesulfonic acid was gradually added by dripping. After the completion of dripping, the mixture was stirred for 30 minutes, followed by heating under reflux for 1 hour. After removing the solvent from the resultant, the resultant was recrystallized with a mixed solvent of ethanol and n-hexane to thereby obtain colorless nonafluorobutanesulfonic acid-2-heptadecylimidazole salt. The yield was 95%.

The FTIR absorbance peaks of the product and the assignments are presented below.

The symmetric stretching vibrations of $SO_2$ were observed at 1,135 $cm^{-1}$, the asymmetric stretching vibrations of the $SO_2$ bonds were observed at 1,356 $cm^{-1}$, the symmetric stretching vibrations of $CF_2$ were observed at 1,238 $cm^{-1}$, the symmetric stretching vibrations of C=N bonds were observed at 1,471 $cm^{-1}$, symmetric stretching vibrations of $CH_2$ were observed at 2,850 $cm^{-1}$, the asymmetric stretching vibrations of $CH_2$ were observed at 2,918 $cm^{-1}$, and the stretching vibrations of NH bonds were observed at 3,160 $cm^{-1}$.

Moreover, peaks of the protons ($^1$H)NMR and carbons ($^{13}$C)NMR in deuterated chloroform are presented below. The peaks of NMR are presented in Table 2, and the assignments were presented below.

$^1$H-NMR (CDCl$_3$, δ ppm): 0.847 (t, 3H, J=6.8 Hz), 1.160-1.340 (m, 28H), 1.710-1.809 (m, 2H), 2.943 (t, J=7.5 Hz, 2H), 7.130 (s, 2H), 11.150 (brs, 2H)

$^{13}$C-NMR (CDCl$_3$, δ ppm): 14.055, 22.663, 25.777, 27.395, 28.875, 28.967, 29.349, 29.379, 29.532, 29.654, 29.684, 31.913, 118.409, 148.584

The product was determined as nonafluorobutanesulfonic acid-2-heptadecylimidazole salt from the spectra above.

Comparative Example 4A

Synthesis of Pentadecafluorooctanoic Acid Octadecyl Ammonium Salt

For comparison, a synthesis of pentadecafluorooctanoic acid octadecyl ammonium salt was performed according to the following scheme.

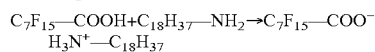

In ethanol, 4.14 g of pentadecafluorooctanoic acid and 2.69 g of octadecylamine were added, and the resultant mixture was heated under reflux for 1 hour. After removing the solvent from the resultant, the resultant was recrystallized with a mixed solvent of n-hexane and ethanol, to thereby obtain 6.23 g of colorless plate crystals. The yield was 92.0%.

The FTIR absorbance peaks of the product and the assignments are presented below.

The symmetric stretching vibrations of $CF_2$ were observed at 1,141 $cm^{-1}$, 1,201 $cm^{-1}$, and 1,232 $cm^{-1}$, the bending vibrations of $CH_2$ were observed at 1,473 $cm^{-1}$, the stretching vibrations of C=O were observed at 1,677 $cm^{-1}$, the symmetric stretching vibrations of $CH_2$ were observed at 2,851 $cm^{-1}$, the asymmetric stretching vibrations of $CH_2$ were observed at 2,918 $cm^{-1}$, and the stretching vibrations of $NH_4^+$ were observed at the range between 3,000 $cm^{-1}$ and 3,325 $cm^{-1}$.

Moreover, peaks of the protons ($^1$H)NMR and carbons ($^{13}$C)NMR in deuterated chloroform are presented below.

$^1$H-NMR (CD$_3$OD, δ ppm): 0.890 (t/J=6.6 Hz, 3H), 1.214-1.408 (m, 30H), 1.590-1.690 (m, 2H), 2.896 (t/J=7.5 Hz, 2H), 4.891 (brs)

$^{13}$C-NMR (CD$_3$OD, δ ppm): 14.444, 23.740, 27.464, 28.578, 30.242, 30.486, 30.516, 30.669, 30.791, 33.081, 40.758

The product was determined as pentadecafluorooctanoic acid octadecyl ammonium salt from the spectra above.

Note that, a pKa of an acid [pentadecafluorooctanoic acid] that was a base of the conjugate base in the pentadecafluorooctanoic acid octadecyl ammonium salt was 12.7 in acetonitrile.

The ionic liquids synthesized in Examples and Comparative Examples above are summarized below.

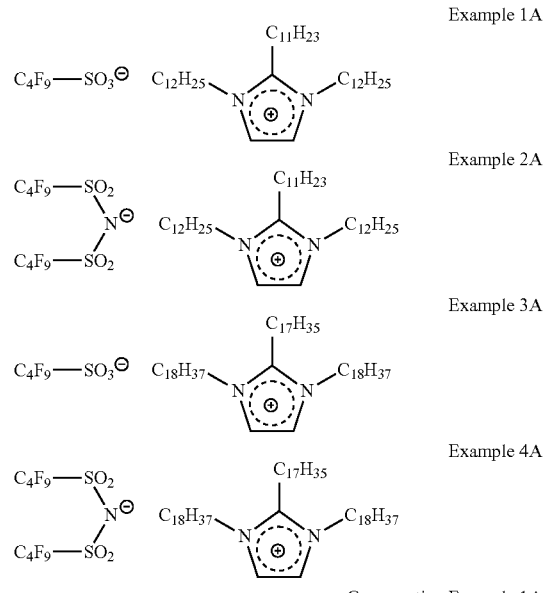

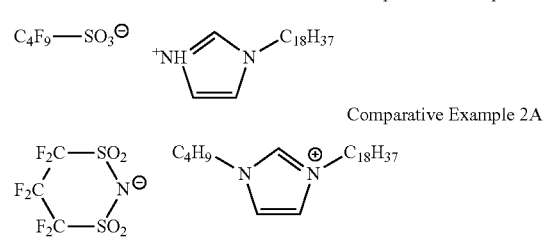

-continued

Comparative Example 3A

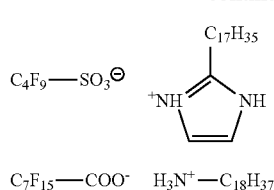

Comparative Example 4A $C_7F_{15}$—COO⁻  $H_3N^+$—$C_{18}H_{37}$

<Solubility Measurement Results to Fluorine-Based Solvent and Hydrocarbon-Based Solvent>

Solubility tests were performed on the ionic liquids synthesized in Examples and Comparative Examples, Z-DOL, and Z-TETRAOL, using, as a fluorine-based solvent, Vertrel XF [$CF_3(CHF)_2CF_2CF_3$] available from Du Pont-Mitsui Fluorochemicals Company, Ltd., and special grade chemical n-hexane available from JUNSEI CHEMICAL CO., LTD.

To a predetermined amount of Vertrel XF or n-hexane, the ionic liquid, Z-DOL, or Z-TETRAOL was added. Ultrasonic waves were applied to the resultant mixture for 5 minutes, followed by leaving the mixture to stand for 1 day. The solubility was visually observed.

Specifically, 0.2 parts by mass of the ionic liquid, Z-DOL, or Z-TETRAOL was added to 100 parts by mass of Vertrel XF (25° C.). After applying ultrasonic waves to the resultant for 5 minutes, the resultant was left to stand for 1 day. Thereafter, the solubility was visually observed and evaluated based on the following evaluation criteria.

In case of n-hexane, similarly, 0.5 parts by mass of the ionic liquid, Z-DOL, or Z-TETRAOL was added to 100 parts by mass of n-hexane at 25° C. After applying ultrasonic waves to the resultant for 5 minutes, the resultant was left to stand for 1 day. Thereafter, the solubility was visually observed and evaluated based on the following evaluation criteria.

[Evaluation Criteria (Fluorine-Based Solvent)]
 0.2% by mass or greater:
  Soluble with addition of 0.2 parts by mass
 Less than 0.2% by mass:
  Insoluble with addition of 0.2 parts by mass

[Evaluation Criteria (Hydrocarbon-Based Solvent)]
 0.5% by mass or greater:
  Soluble with addition of 0.5 parts by mass
 Less than 0.5% by mass:
  Insoluble with addition of 0.5 parts by mass Note that, the solubility was visually observed, and it was judged as soluble when it was transparent. Moreover, it was judged as not soluble (insoluble) when it was opaque or insoluble components were observed.

The results are presented in Table 2.

TABLE 2

| | Synthesized product | Structure | Solubility Vertrel XF | Solubility n-hexane |
|---|---|---|---|---|
| Ex. 1B | Ex. 1A | nonafluorobutanesulfonic acid-1,3-didodecyl-2-undecylimidazolium | 0.2% by mass or greater | 0.5% by mass or greater |
| Ex. 2B | Ex. 2A | bis(nonafluorobutanesulfonyl)imide-1,3-didodecyl-2-undecylimidazolium | 0.2% by mass or greater | 0.5% by mass or greater |
| Ex. 3B | Ex. 3A | nonafluorobutanesulfonic acid-1,3-dioctadecyl-2-heptadecylimidazolium | less than 0.2% by mass | 0.5% by mass or greater |
| Ex. 4B | Ex. 4A | bis(nonafluorobutanesulfonyl)imide-1,3-dioctanedecyl-2-heptadecylimidazolium | less than 0.2% by mass | 0.5% by mass or greater |
| Comp. Ex. 1B | Comp. Ex. 1A | nonafluorobutanesulfonic acid-1-octadecylimidazolium | less than 0.2% by mass | less than 0.5% by mass |
| Comp. Ex. 2B | Comp. Ex. 2A | hexafluorocyclopropane-1,3-bis(sulfonyl)imide-1-butyl-3-n-octadecylimidazolium | less than 0.2% by mass | less than 0.5% by mass |
| Comp. Ex. 3B | Comp. Ex. 3A | nonafluorobutanesulfonic acid-2-heptadecylimidazole salt | less than 0.2% by mass | less than 0.5% by mass |
| Comp. Ex. 4B | Comp. Ex. 4A | pentadecafluorooctanoic acid octadecyl ammonium salt | less than 0.2% by mass | less than 0.5% by mass |
| Comp. Ex. 5B | | Z-DOL | 0.2% by mass or greater | less than 0.5% by mass |
| Comp. Ex. 6B | | Z-TETRAOL | 0.2% by mass or greater | less than 0.5% by mass |

The solubility of the ionic liquid of Example 1A to Vertrel XF was 0.2% by mass or greater, and the solubility of the ionic liquid of Example 1A to n-hexane was 0.5% by mass or greater.

The solubility of the ionic liquid of Example 2A to Vertrel XF was 0.2% by mass or greater, and the solubility of the ionic liquid of Example 2A to n-hexane was 0.5% by mass or greater.

The solubility of the ionic liquid of Example 3A to Vertrel XF was less than 0.2% by mass, and the solubility of the ionic liquid of Example 3A to n-hexane was 0.5% by mass or greater.

The solubility of the ionic liquid of Example 4A to Vertrel XF was less than 0.2% by mass, and the solubility of the ionic liquid of Example 4A to n-hexane was 0.5% by mass or greater.

The solubility of each of the ionic liquids of Comparative Examples 1A to 4A to Vertrel XF was less than 0.2% by mass, and the solubility of each of the ionic liquids of Comparative Examples 1A to 4A to n-hexane was less than 0.5% by mass. The solubility of each of Z-DOL and Z-TET- RAOL to Vertrel XF was 0.2% by mass or greater, but the solubility of each of Z-DOL and Z-TETRAOL to n-hexane was less than 0.5% by mass.

It was found from the result above that the ionic liquids of Examples had improved solubility to the hydrocarbon-based solvent. The result as mentioned means that each ionic liquid exhibits an effect as an additive considering that a material widely used as a lubricant is long-chain fatty acid or an ester of long-chain fatty acid. In Examples 1A to 2A where used were the imidazole derivatives the lengths of hydrocarbon of which were 11 and 12, respectively, moreover, the solubility was improved against Vertrel XF, which was a fluorine-based solvent, and the ionic liquids of Examples 1A and 2A were sufficient as being used for hard disks.

It was found from Comparative Examples 1B to 3B that the imidazole-based ionic liquid having one carbon chain or the imidazole-based ionic liquid having two carbon chains but one of which was short and includes 4 carbon atoms had low solubility to the fluorine-based solvent and the hydrocarbon-based solvent. Moreover, it could be understood that the solubility was significantly improved by introducing 3 or more long-chain hydrocarbons. Specifically, it can be understood that it is effective for solubility to solvents by introducing 3 or more long-chain hydrocarbons as a molecule design method.

As a result of the researches of the present inventors, it was found that solubility of the ionic liquid to the hydrocarbon-based solvent was improved by introducing 3 or more long-chain hydrocarbons to the ionic liquid.

Example 1C

<Measurement Result of Thermal Stability>

The 5% weight reduction temperature, 10% weight reduction temperature, and 20% weight reduction temperature of nonafluorobutanesulfonic acid-1,3-didodecyl-2-undecylimidazolium were 287.9° C., 331.8° C., and 378.4° C., respectively, and were higher than the commercial products presented as Comparative Examples, perfluoropolyether Z-DOL (Comparative Example 5C) by 130° C. or greater, and higher than Z-TETRAOL (Comparative Example 6C) by 40° C. or greater, which were known as common lubricants for magnetic recording media.

Example 2C

<Measurement Result of Thermal Stability>

The 5% weight reduction temperature, 10% weight reduction temperature, and 20% weight reduction temperature of bis(nonafluorobutanesulfonyl)imide-1,3-didodecyl-2-undecylimidazolium were 335.7° C., 368.9° C., and 395.7° C., respectively. Compared with the commercial products, perfluoropolyether Z-DOL (Comparative Example 5C) and Z-TETRAOL (Comparative Example 6C), it was found that the thermal stability was improved by 170° C. or greater, and 90° C. or greater, respectively.

Example 3C

<Measurement Result of Thermal Stability>

The 5% weight reduction temperature, 10% weight reduction temperature, and 20% weight reduction temperature of nonafluorobutanesulfonic acid-1,3-dioctadecyl-2-heptadecylimidazolium were 279.7° C., 310.9° C., and 361.9° C., respectively. Compared with the commercial products, perfluoropolyether Z-DOL (Comparative Example 5C) and Z-TETRAOL (Comparative Example 6C), it was found that the thermal stability was improved by 110° C. or greater, and 40° C. or greater, respectively.

Example 4C

<Measurement Result of Thermal Stability>

The 5% weight reduction temperature, 10% weight reduction temperature, and 20% weight reduction temperature of bis(nonafluorobutanesulfonyl)imide-1,3-dioctadecyl-2-heptadecylimidazolium were 300.1° C., 337.3° C., and 385.8° C., respectively. Compared with the commercial products, perfluoropolyether Z-DOL (Comparative Example 5C) and Z-TETRAOL (Comparative Example 6C), it was found that the thermal stability was improved by 140° C. or greater, and 60° C. or greater, respectively.

Comparative Example 1C

<Measurement Result of Thermal Stability>

The 5% weight reduction temperature, 10% weight reduction temperature, and 20% weight reduction temperature of nonafluorobutanesulfonic acid-1-octadecylimidazolium were 349.3° C., 375.0° C., and 397.5° C., respectively. Since the nonafluorobutanesulfonic acid-1-octadecylimidazolium was an ionic liquid, the thermal stability was high compared with the commercial products, perfluoropolyether Z-DOL (Comparative Example 5C) and Z-TETRAOL (Comparative Example 6C).

Comparative Example 2C

<Measurement Result of Thermal Stability>

The 5% weight reduction temperature, 10% weight reduction temperature, and 20% weight reduction temperature of hexafluorocyclopropane-1,3-bis(sulfonyl)imide-1-butyl-3-n-octadecylimidazole were 347.2° C., 367.0° C., and 387.8° C., respectively. Since the hexafluorocyclopropane-1,3-bis(sulfonyl)imide-1-butyl-3-n-octadecylimidazole was an ionic liquid, the thermal stability was high compared with the commercial products, perfluoropolyether Z-DOL (Comparative Example 5C) and Z-TETRAOL (Comparative Example 6C).

Comparative Example 3C

<Measurement Result of Thermal Stability>

The 5% weight reduction temperature, 10% weight reduction temperature, and 20% weight reduction temperature of nonafluorobutanesulfonic acid-2-heptadecylimidazole salt were 365.4° C., 390.5° C., and 414.3° C., respectively. Since the nonafluorobutanesulfonic acid-2-heptadecylimidazole salt was an ionic liquid, the thermal stability was high compared with the commercial products, perfluoropolyether Z-DOL (Comparative Example 5C) and Z-TETRAOL (Comparative Example 6C).

Comparative Example 4C

<Measurement Result of Thermal Stability>

The 5% weight reduction temperature, 10% weight reduction temperature, and 20% weight reduction temperature of pentadecafluorooctanoic acid octadecyl ammonium salt were 206.9° C., 215.8° C., and 223.4° C., respectively. Although the pentadecafluorooctanoic acid octadecyl ammonium salt was an ionic liquid, the bonding strength between ions was weak because the pKa of the acid was greater than 10, and hence the pentadecafluorooctanoic acid octadecyl ammonium salt lacked thermal stability. In case of Comparative Example 4C, the pentadecafluorooctanoic acid octadecyl ammonium salt was an ionic liquid, but the thermal stability did not significantly improve compared to the commercial products, perfluoropolyether Z-DOL (Comparative Example 5C) and Z-TETRAOL (Comparative Example 6C).

Comparative Example 5C

<Measurement Result of Thermal Stability>
A measurement of a commercial product perfluoropolyether Z-DOL having a hydroxyl group at a terminal and a molecular weight of about 2,000 as Comparative Example 5C was performed. As a result, the 5% weight reduction temperature, 10% weight reduction temperature, and 20% weight reduction temperature of Z-DOL were 165.0° C., 197.0° C., and 226.0° C., respectively. The weight reduction was caused by evaporation.

Comparative Example 6C

<Measurement Result of Thermal Stability>
Perfluoropolyether (Z-TETRAOL) having a few hydroxyl groups at a terminal and a molecular weight of about 2,000, which was a commercial product and typically used as a lubricant for magnetic recording media was used as a lubricant of Comparative Example 6C. The 5% weight reduction temperature, 10% weight reduction temperature, and 20% weight reduction temperature of Z-TETRAOL were 240.0° C., 261.0° C., and 282.0° C., respectively. Similarly to Z-DOL, the weight reduction was caused by evaporation.

The results of Examples 1C to 4C and Comparative Examples 1C to 6C are summarized in Table 3.

TABLE 3

| Example | Synthesis Example or Compound Name | Weight reduction temperature (° C.) | | | Melting point (° C.) |
|---|---|---|---|---|---|
| | | 5% | 10% | 20% | |
| Ex. 1C | Ex. 1A | 287.9 | 331.8 | 378.4 | 78.4 |
| Ex. 2C | Ex. 2A | 335.7 | 368.9 | 395.7 | 76.0 |
| Ex. 3C | Ex. 3A | 279.7 | 310.9 | 361.9 | 57.2 |
| Ex. 4C | Ex. 4A | 300.1 | 337.3 | 385.8 | 83.0 |
| Comp. Ex. 1C | Comp. Ex. 1A | 349.3 | 375.0 | 397.5 | 86.2 |
| Comp. Ex. 2C | Comp. Ex. 2A | 347.2 | 367.0 | 387.8 | 55.8 |
| Comp. Ex. 3C | Comp. Ex. 3A | 365.4 | 390.5 | 414.3 | 60.6 |
| Comp. Ex. 4C | Comp. Ex. 4A | 206.9 | 215.8 | 223.4 | 61.7 |
| Comp. Ex. 5C | Z-DOL | 165.0 | 197.0 | 226.0 | <25.0 |
| Comp. Ex. 6C | Z-TETRAOL | 240.0 | 261.0 | 282.0 | <25.0 |

As presented above, it could be understood that the lubricants of imidazole-based ionic liquids having long-chain hydrocarbon groups had significantly excellent heat stability compared to the perfluoropolyether of the commercial products of Comparative Examples 5C and 6C. As described earlier, the ionic liquid of Comparative Example 4C lacked thermal stability because the ionic liquid has high pKa of the acid because the acid was carboxylic acid, and thus bonding strength between ions was weak.

A systematic difference could not be found when the thermal stability was compared between the imidazole-based ionic liquids including long-chain hydrocarbon groups, but the imidazole-based ionic liquid had sufficient thermal stability.

Examples 1D to 4D and Comparative Examples 1D to 3D

<Disk Durability Test>
Magnetic disks were produced by applying lubricants including the ionic liquids of Examples 1A to 4A and Comparative Examples 1A to 3A, respectively. As presented in Table 4, the CSS measurements of the magnetic disks were greater than 50,000 times, and the CSS measurements after the heating test were also greater than 50,000 times, and the magnetic disks exhibited excellent durability.

Comparative Example 4D

<Disk Durability Test>
The magnetic disk was produced using a lubricant including pentadecafluorooctanoic acid octadecyl ammonium salt. As presented in Table 4, the CSS measurement of the magnetic disk was greater than 50,000 times but the CSS measurement of the heating test was 891 times and the durability of the magnetic disk was deteriorated by the heating test. As presented with Comparative Example 4C, the pentadecafluorooctanoic acid octadecyl ammonium salt was an ionic liquid, but the pKa of the acid was greater than 10. Therefore, the bonding strength between ions was weak and the thermal stability was deteriorated, and therefore it was considered that the properties after the heating test were deteriorated.

Comparative Example 5D

<Disk Durability Test>
The magnetic disk was produced using a lubricant including Z-DOL. As presented in Table 4, the CSS measurement of the magnetic disk was greater than 50,000 times but the CSS measurement of the heating test was the CSS measurement of the heating test was 12,000 times and the durability of the magnetic disk was deteriorated by the heating test.

Comparative Example 6D

<Disk Durability Test>
The magnetic disk was produced using a lubricant including Z-TETRAOL. As presented in Table 4, the CSS measurement of the magnetic disk was greater than 50,000 times but the CSS measurement of the heating test was the CSS measurement of the heating test was 36,000 times and the durability of the magnetic disk was deteriorated by the heating test.

The results of Examples 1D to 4D, and Comparative Examples 1D to 6D are summarized in Table 4.

TABLE 4

| Example | Synthesis Example or Compound Name | CSS durability | | CSS durability after heating | |
|---|---|---|---|---|---|
| Ex. 1D | Ex. 1A | 25° C., 60% RH | >50,000 | 25° C., 60% RH | >50,000 |
| Ex. 2D | Ex. 2A | 25° C., 60% RH | >50,000 | 25° C., 60% RH | >50,000 |
| Ex. 3D | Ex. 3A | 25° C., 60% RH | >50,000 | 25° C., 60% RH | >50,000 |
| Ex. 4D | Ex. 4A | 25° C., 60% RH | >50,000 | 25° C., 60% RH | >50,000 |

TABLE 4-continued

| Example | Synthesis Example or Compound Name | CSS durability | | CSS durability after heating | |
|---|---|---|---|---|---|
| Comp. Ex. 1D | Comp. Ex. 1A | 25° C., 60% RH | >50,000 | 25° C., 60% RH | >50,000 |
| Comp. Ex. 2D | Comp. Ex. 2A | 25° C., 60% RH | >50,000 | 25° C., 60% RH | >50,000 |
| Comp. Ex. 3D | Comp. Ex. 3A | 25° C., 60% RH | >50,000 | 25° C., 60% RH | >50,000 |
| Comp. Ex. 4D | Comp. Ex. 4A | 25° C., 60% RH | >50,000 | 25° C., 60% RH | 891 |
| Comp. Ex. 5D | Z-DOL | 25° C., 60% RH | >50,000 | 25° C., 60% RH | 12,000 |
| Comp. Ex. 6D | Z-TETRAOL | 25° C., 60% RH | >50,000 | 25° C., 60% RH | 36,000 |

Examples 1E to 4E and Comparative Examples 1E to 6E

After producing magnetic tapes using lubricants including the ionic liquids of Examples 1A to 4A, the ionic liquids of Comparative Examples 1A to 4A, Z-DOL, and Z-Tetraol, respectively, the following measurements were performed.

Coefficient of Friction of Magnetic Tape after Shuttle Run of 100 Times:

In the environment having a temperature of −5° C., or in the environment having a temperature of 40° C. and relative humidity of 90%.

Still Durability Test:
In the environment having a temperature of −5° C., or in the environment having a temperature of 40° C. and relative humidity of 30%.

Shuttle Durability Test:
In the environment having a temperature of −5° C., or in the environment having a temperature of 40° C. and relative humidity of 90%.

Coefficient of Friction of Magnetic Tape after Shuttle Run of 100 Times after Heating Test:
In the environment having a temperature of −5° C., or in the environment having a temperature of 40° C. and relative humidity of 90%.

Still Durability Test after Heating Test:
In the environment having a temperature of −5° C., or in the environment having a temperature of 40° C. and relative humidity of 30%.

Shuttle Durability Test after Heating Test:
In the environment having a temperature of −5° C., or in the environment having a temperature of 40° C. and relative humidity of 90%.

The results of Examples 1E to 4E and Comparative Examples 1E to 6E are summarized in Tables 5-1 and 5-2.

TABLE 5-1

| | Coefficient of friction after 100 runs | | Still durability/ min | | Shuttle durability/ times | | Coefficient of friction after 100 runs after heating test | | Still durability after heating test/ min | | Shuttle durability after heating/ times | |
|---|---|---|---|---|---|---|---|---|---|---|---|---|
| Ex. 1E | −5° C. | 0.20 | −5° C. | >60 | −5° C. | >200 | −5° C. | 0.21 | −5° C. | >60 | −5° C. | >200 |
| | 40° C., 90% RH | 0.21 | 40° C., 30% RH | >60 | 40° C., 90% RH | >200 | 40° C., 90% RH | 0.22 | 40° C., 30% RH | >60 | 40° C., 90% RH | >200 |
| Ex. 2E | −5° C. | 0.21 | −5° C. | >60 | −5° C. | >200 | −5° C. | 0.22 | −5° C. | >60 | −5° C. | >200 |
| | 40° C., 90% RH | 0.22 | 40° C., 30% RH | >60 | 40° C., 90% RH | >200 | 40° C., 90% RH | 0.23 | 40° C., 30% RH | >60 | 40° C., 90% RH | >200 |
| Ex. 3E | −5° C. | 0.17 | −5° C. | >60 | −5° C. | >200 | −5° C. | 0.18 | −5° C. | >60 | −5° C. | >200 |
| | 40° C., 90% RH | 0.18 | 40° C., 30% RH | >60 | 40° C., 90% RH | >200 | 40° C., 90% RH | 0.18 | 40° C., 30% RH | >60 | 40° C., 90% RH | >200 |
| Ex. 4E | −5° C. | 0.18 | −5° C. | >60 | −5° C. | >200 | −5° C. | 0.19 | −5° C. | >60 | −5° C. | >200 |
| | 40° C., 90% RH | 0.19 | 40° C., 30% RH | >60 | 40° C., 90% RH | >200 | 40° C., 90% RH | 0.19 | 40° C., 30% RH | >60 | 40° C., 90% RH | >200 |

TABLE 5-2

| | Coefficient of friction after 100 runs | | Still durability/ min | | Shuttle durability/ times | | Coefficient of friction after 100 runs after heating test | | Still durability after heating test/ min | | Shuttle durability after heating/ times | |
|---|---|---|---|---|---|---|---|---|---|---|---|---|
| Comp. Ex. 1E | −5° C. | 0.20 | −5° C. | >60 | −5° C. | >200 | −5° C. | 0.2 | −5° C. | >60 | −5° C. | >200 |
| | 40° C., 90% RH | 0.22 | 40° C., 30% RH | >60 | 40° C., 90% RH | >200 | 40° C., 90% RH | 0.2 | 40° C., 30% RH | >60 | 40° C., 90% RH | >200 |
| Comp. Ex. 2E | −5° C. | 0.23 | −5° C. | >60 | −5° C. | >200 | −5° C. | 0.3 | −5° C. | >60 | −5° C. | >200 |
| | 40° C., 90% RH | 0.25 | 40° C., 30% RH | >60 | 40° C., 90% RH | >200 | 40° C., 90% RH | 0.3 | 40° C., 30% RH | >60 | 40° C., 90% RH | >200 |
| Comp. Ex. 3E | −5° C. | 0.18 | −5° C. | >60 | −5° C. | >200 | −5° C. | 0.2 | −5° C. | >60 | −5° C. | >200 |
| | 40° C., 90% RH | 0.20 | 40° C., 30% RH | >60 | 40° C., 90% RH | >200 | 40° C., 90% RH | 0.2 | 40° C., 30% RH | >60 | 40° C., 90% RH | >200 |
| Comp. Ex. 4E | −5° C. | 0.21 | −5° C. | >60 | −5° C. | >200 | −5° C. | 0.5 | −5° C. | 12 | −5° C. | 30 |
| | 40° C., 90% RH | 0.25 | 40° C., 30% RH | >60 | 40° C., 90% RH | >200 | 40° C., 90% RH | 0.5 | 40° C., 30% RH | 16 | 40° C., 90% RH | 23 |
| Comp. Ex. 5E | −5° C. | 0.25 | −5° C. | 12 | −5° C. | 59 | −5° C. | 0.3 | −5° C. | 12 | −5° C. | 46 |
| | 40° C., 90% RH | 0.30 | 40° C., 30% RH | 48 | 40° C., 90% RH | 124 | 40° C., 90% RH | 0.4 | 40° C., 30% RH | 15 | 40° C., 90% RH | 58 |
| Comp. Ex. 6E | −5° C. | 0.22 | −5° C. | 25 | −5° C. | 65 | −5° C. | 0.3 | −5° C. | 23 | −5° C. | 55 |
| | 40° C., 90% RH | 0.26 | 40° C., 30% RH | 35 | 40° C., 90% RH | 156 | 40° C., 90% RH | 0.3 | 40° C., 30% RH | 31 | 40° C., 90% RH | 126 |

In the tables, ">60" of the still durability denotes greater than 60 minutes.

In the tables, ">200" of the shuttle durability denotes greater than 200 times.

The following facts were confirmed.

It was found that the magnetic tapes to which the lubricants including the ionic liquids of Examples 1A to 4A were applied, respectively, had excellent friction resistance, still durability, and shuttle durability.

It was found that the magnetic tapes to which the lubricants including the ionic liquids of Comparative Examples 1A to 3A were applied, respectively, had excellent friction resistance, still durability, and shuttle durability. Since the lubricants in Comparative Examples 1A to 3A were the ionic liquids, the magnetic tapes had excellent durability even after the heating test.

It was found that the magnetic tape to which the lubricant including the ionic liquid of Comparative Example 4A was applied had excellent friction resistance, still durability, and shuttle durability. The lubricant in Comparative Example 4A caused significant deterioration of the magnetic tape after the heating test.

It was found that the magnetic tape to which Z-DOL was applied had significant deterioration in still durability and shuttle durability.

It was found that the magnetic tape to which Z-Tetraol was applied had significant deterioration in still durability and shuttle durability.

It was found from Tables 5-1 and 5-2 that excellent heat resistance, and durability of the magnetic tape and magnetic disk could be obtained when the lubricant included the ionic liquid including a conjugate base and a conjugate acid, the conjugate acid was represented by General Formula (A), and a pKa of an acid that was a source of the conjugate base was 10 or less in acetonitrile. Not only achieving excellent thermal resistance and durability of a magnetic recording medium, such a lubricant dissolved to n-hexane as a diluent as well as the ionic liquid, which meant that the lubricant could exhibit an effect as an additive to long-chain fatty acid or ester of long-chain fatty acid, which were widely used as lubricants. Among such lubricants, there were lubricants soluble to Vertrel that was a fluorine-based solvent, and thus used of such lubricants on production process was not problem, particularly when the lubricants were used for hard disks.

As it is clear from the descriptions above, an ion liquid-based lubricant, which includes an ionic liquid including a conjugate base and a conjugate acid, where the conjugate acid is represented by General Formula (A) and a pKa of an acid that is a source of the conjugate base is 10 or less in acetonitrile, has a high decomposition temperature, and high 5%, 10%, and 20% weight reduction temperatures, and has excellent thermal stability. Moreover, the lubricant can maintain excellent lubricity under high temperature conditions compared to conventional perfluoropolyester, and can maintain lubricity over a long period. Accordingly, a magnetic recording medium using the lubricant including the ionic liquid can obtain excellent running performances, abrasion resistance, and durability.

This application claims priority to Japanese application No. 2016-080576, filed on Apr. 13, 2016 and incorporated herein by reference.

What is claimed is:

1. A lubricant comprising:
an ionic liquid including a conjugate base and a conjugate acid,
wherein the conjugate acid is represented by General Formula (A) below, and
wherein a pKa of an acid that is a source of the conjugate base in acetonitrile is 10 or less, General Formula (A)

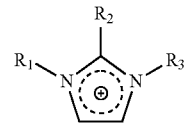

where, in General Formula (A), $R_1$, $R_2$, and $R_3$ are each independently a group including a hydrocarbon group having 10 or greater carbon atoms.

2. The lubricant according to claim 1,
wherein the conjugate base is represented by General Formula (X) or General Formula (Y) below, General Formula (X)

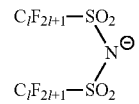

General Formula (Y)

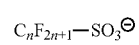

where, in General Formula (X), l is an integer of 1 or greater but 12 or less, and
where, in General Formula (Y), n is an integer of 1 or greater but 12 or less.

3. A magnetic recording medium comprising:
a non-magnetic support;
a magnetic layer disposed on the non-magnetic support; and
the lubricant according to claim 1, disposed on the magnetic layer.

4. An ionic liquid comprising:
a conjugate base; and
a conjugate acid,
wherein the conjugate acid is represented by General Formula (A) below, and
wherein a pKa of an acid that is a source of the conjugate base in acetonitrile is 10 or less, General Formula (A)

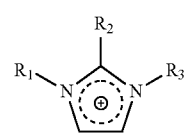

where, in General Formula (A), $R_1$, $R_2$, and $R_3$ are each independently a group including a hydrocarbon group having 10 or greater carbon atoms.

5. The ionic liquid according to claim 4,
wherein the conjugate base is represented by General Formula (X) or General Formula (Y) below, General Formula (X)

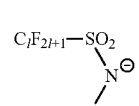

General Formula (Y)

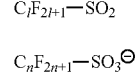

where, in General Formula (X), l is an integer of 1 or greater but 12 or less, and where, in General Formula (Y), n is an integer of 1 or greater but 12 or less.

6. The lubricant according to claim 1, wherein the conjugate acid is represented by one of structures below:

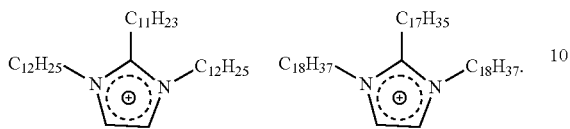

7. The lubricant according to claim 1, wherein the conjugate base is represented by one of structures below:

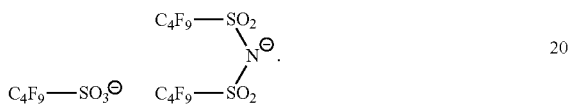

8. The ionic liquid according to claim 4, wherein the conjugate acid is represented by one of structures below:

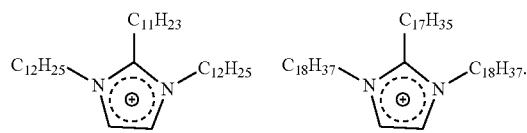

9. The ionic liquid according to claim 4, wherein the conjugate base is represented by one of structures below:

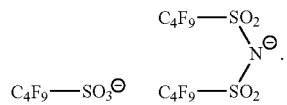

* * * * *